US010485563B2

(12) United States Patent
Honda et al.

(10) Patent No.: US 10,485,563 B2
(45) Date of Patent: Nov. 26, 2019

(54) CALCULUS/CALCULI RETRIEVING DEVICE AND METHOD

(71) Applicant: TERUMO KABUSHIKI KAISHA, Shibuya-ku, Tokyo (JP)

(72) Inventors: Kei Honda, Hadano (JP); Makoto Jinno, Tokyo (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 614 days.

(21) Appl. No.: 14/671,083

(22) Filed: Mar. 27, 2015

(65) Prior Publication Data

US 2016/0278795 A1 Sep. 29, 2016

(51) Int. Cl.
*A61B 17/22* (2006.01)
*A61B 17/00* (2006.01)

(52) U.S. Cl.
CPC ...... *A61B 17/22* (2013.01); *A61B 2017/0034* (2013.01); *A61B 2017/00296* (2013.01); *A61B 2017/00331* (2013.01); *A61B 2017/00553* (2013.01); *A61B 2017/00738* (2013.01); *A61B 2017/22035* (2013.01); *A61B 2017/22079* (2013.01); *A61B 2217/005* (2013.01)

(58) Field of Classification Search
CPC .......... A61B 17/22; A61B 2017/00296; A61B 2217/005; A61B 2017/00331; A61B 2017/00553; A61B 2017/22035; A61B 2017/003; A61B 2017/00305; A61B 2017/00314; A61B 2017/00738; A61B 2017/2927; A61B 1/00089; A61B 1/00098
See application file for complete search history.

(56) References Cited

U.S. PATENT DOCUMENTS

| 4,243,040 A | * | 1/1981 | Beecher | A61B 17/22032 604/271 |
| 4,292,971 A | * | 10/1981 | Smit | A61F 7/02 604/23 |
| 4,807,626 A | * | 2/1989 | McGirr | A61B 17/221 600/436 |
| 6,143,009 A | * | 11/2000 | Shiber | A61B 17/320758 606/159 |
| 6,702,830 B1 | * | 3/2004 | Demarais | A61B 17/320725 604/22 |

(Continued)

*Primary Examiner* — Ryan J. Severson
*Assistant Examiner* — Christian D Knauss
(74) *Attorney, Agent, or Firm* — Buchanan Ingersoll & Rooney PC

(57) ABSTRACT

A method of retrieving calculus in a living body and relocating the calculus to a different location in the living body involves positioning an elongated member in the living body in which the calculus is located, drawing the calculus in the living body toward the elongated member while the elongated member is positioned in the living body so that the calculus is retained by the elongated member; moving the elongated member so that the elongated member is located at a position in the living body that is different from the position of the elongated member in the living body during the drawing of the calculus toward the elongated member; and releasing the calculus from the elongated member so that the calculus is at a position in the living body different from a location of the calculus in the living body while the calculus is being drawn toward the elongated member.

19 Claims, 15 Drawing Sheets

(56) References Cited

U.S. PATENT DOCUMENTS

2004/0019358 A1* 1/2004 Kear ............... A61B 17/22031
606/127
2006/0229659 A1* 10/2006 Gifford ............... A61B 18/02
606/200

* cited by examiner

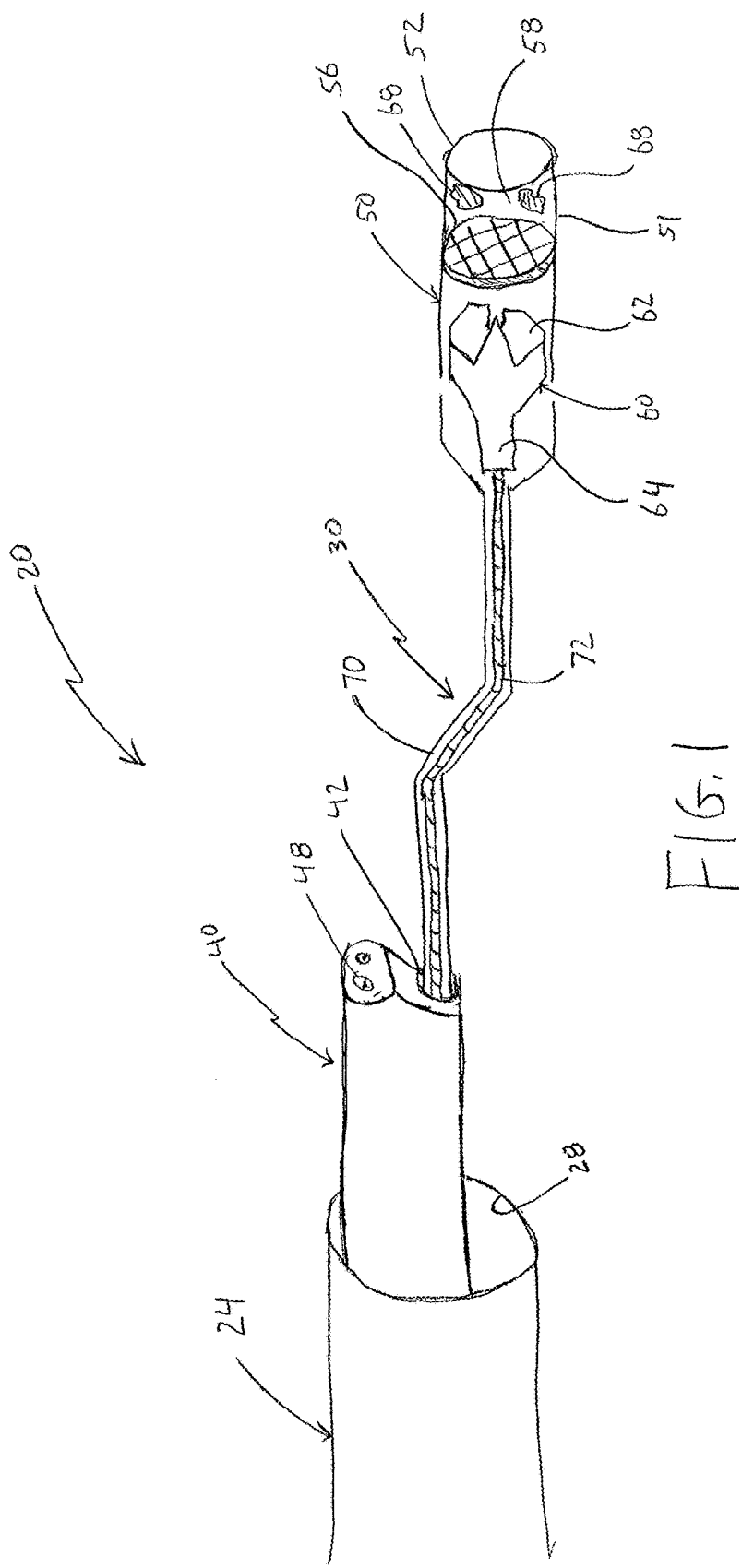

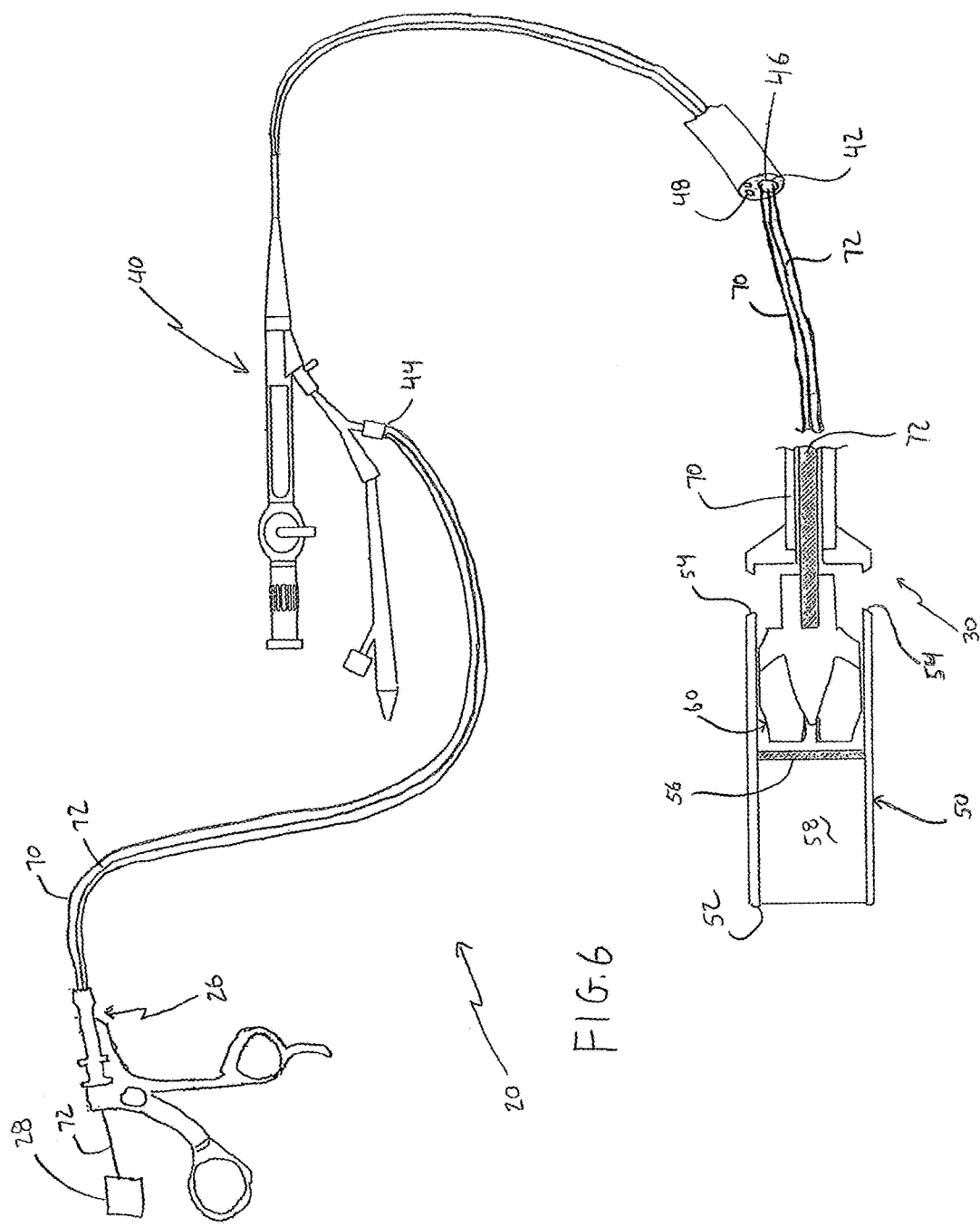

CALCULUS/CALCULI RETRIEVING DEVICE AND METHOD

CROSS-REFERENCE TO OTHER APPLICATIONS

This application discloses subject matter related to subject matter described in U.S. application Ser. No. 14/222,021, U.S. application Ser. No. 14/221,954 and U.S. application Ser. No. 14/221,858, the entire content of each of which is incorporated herein by reference.

TECHNICAL FIELD

The present invention generally pertains to methods, systems and devices for retrieving a mass from a human body. More specifically, the invention involves methods, devices and systems for retrieving stone(s) (e.g., calculus or calculi) from a portion of a human body, and moving the retrieved stone(s) to a different location in the living body.

BACKGROUND DISCUSSION

The term urinary calculus (e.g., kidney stones and ureteral stones) refers to masses or stones, typically solid particles, that form in the human body and are located in the kidneys and/or the ureter. Calculus can exhibit a variety of chemical compositions including calcium oxalate, calcium phosphate, uric acid, cystine, and struvite.

Stone disease (e.g., kidney stones and ureteral stones) is a relatively common urological disorder. The presence of calculus in the body can manifest itself in a variety of ways and can produce a number of medical ailments. For example, the presence of calculus in the renal pelvis and/or the renal calix (i.e., the lumen of the kidney) can cause blood in the urine, urinary obstruction, infection, and various degrees of pain ranging from vague frank pain to much more severe pain not capable of being relieved through general pain medication. The presence of stones or calculi in the ureter can result in relatively severe side and back pain, pain below the ribs, and pain that sometimes spreads to the lower abdomen and groin, as well as pain during urination and hematuria.

Fortunately, many calculi or stones pass out of the body without requiring any specific medical intervention. In those situations where the calculus does not naturally pass out of the body, a medical procedure may be required.

In the past, three main treatments have been used to treat or address calculus or kidney stones. These include shock wave lithotripsy (ESWL), transurethral lithotripsy or ureteroscopy (URS), and percutaneous nephrouretero lithotripsy (PCNL) which is sometimes also referred to as percutaneous nephrolithotomy (PCN).

Shock wave lithotripsy is performed as an extracorporeal treatment. This treatment utilizes a machine called a lithotripter that operates by directing ultrasonic or shock waves from outside the body, through the skin and tissue, and at the calculi or stones. Repeated shock waves apply stress to the stones, eventually breaking the individual stones into smaller pieces which can more easily pass through the urinary tract in urine. One benefit associated with shock wave lithotripsy is that it is a rather simple procedure. But it has been found that there is a relatively high rate of kidney stone recurrence following shock wave lithotripsy.

Transurethral lithotripsy or ureteroscopy represents one such alternative form of treatment. This treatment involves the use of small fiber optic instrument called a ureteroscope which allows access to the calculus in the ureter or kidney. The ureteroscope can be a rigid ureteroscope or more commonly, a flexible ureteroscope. The ureteroscope allows the medical professional to visualize the stone as the ureteroscope moves along the ureter or enters the kidney by way of the bladder and the urethra. Once the calculus is visualized, a basket-like device is used to grasp smaller stones and remove them. If the calculus is excessively large to remove as a single piece, it can be broken into a smaller pieces by using laser energy.

The third form of treatment is percutaneous nephrolithotomy. This procedure is often used with relatively larger calculus that cannot be effectively treated with either ESWL or URS. Percutaneous nephrolithotomy involves nephrostomy; making an incision at the appropriate location, needling by paracentesis needle, positioning a guide wire through the paracentesis needle's lumen into the kidney under radiographic guidance, and then expanding perforated site. A nephroscope is then moved into the kidney via nephrostomy to visualize the calculus. Fragmentation of the calculus can be performed using an ultrasonic probe or laser.

Though these procedures have been commonly used, they are susceptible of certain short comings. For example, the calculus may be located at a place in the living body that is not conducive to treatment by lithotripsy. The calculus may be located in a region of damaged tissue and/or may be located in a small space that is difficult to access with appropriate instrumentation.

SUMMARY

One aspect of the disclosure here involves a method of retrieving calculus in a living body and relocating the calculus to a different location in the living body. The method comprises: positioning an elongated member, which includes a suction head disposed on a distal side of the elongated member, in the living body in which the calculus is located, drawing the calculus in the living body toward the suction head while the suction head is positioned in the living body so that the calculus is retained by the suction head, moving the suction head so that the suction head is located at a position in the living body that is different from the position of the suction head in the living body during the drawing of the calculus toward the suction head, and releasing the calculus from the suction head so that the calculus is at a position in the living body different from a location of the calculus in the living body while the calculus is being drawn toward the suction head.

According to another aspect, a device for retrieving calculus in a lumen of a living body comprises: an elongated member sized to be positioned in the lumen of the living body, the elongated member including a suction head housing disposed on a distal side of the elongated member; a rotatable member positioned inside the elongated member; a shaft connected to the rotatable member so that the shaft and the rotatable member move together as a unit, the shaft being connectable to a drive source to rotate the shaft and the rotatable member, with rotation of the rotatable member creating suction that draws calculus toward the elongated member; a shaft cover possessing a distal end portion having a central axis and a proximal end portion having a central axis, the shaft cover covering the shaft and being connected to the elongated member so that the elongated member and the shaft cover axially move and rotate together; and the central axis of the distal end portion of the shaft cover is offset from the central axis of the proximal end portion of the shaft cover.

Other features and aspects of the calculus retrieving device and method disclosed here will become more apparent from the following detailed description considered with reference to the accompanying drawing figures in which like elements are designated by like reference numerals.

BRIEF DESCRIPTION OF DRAWINGS

FIG. 1 is a schematic illustration of a system useful to retrieve calculus/calculi, including a retrieving device connected to an operation member (not shown in FIG. 1) through the intermediary of a lumen in an elongated body.

FIG. 6 is a schematic illustration of the retrieving system, including the retrieving device connected to the operation member through the intermediary of an elongated body such as a ureteroscope.

DETAILED DESCRIPTION

Figure 3:
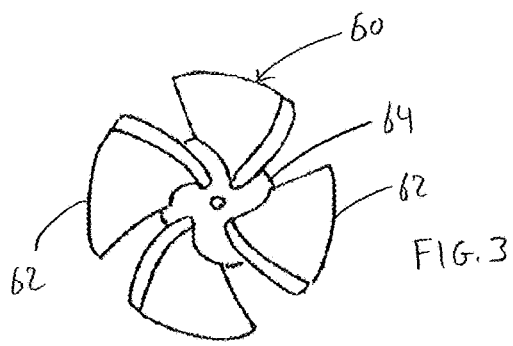
FIG. 3 is a front view of the impeller forming a part of the retrieving device shown in FIG. 2.

Set forth below is a detailed description of features and aspects of the retrieving system, device and method described here as examples of the disclosed invention. The methods, systems, and devices disclosed here for retrieving have particularly useful application to retrieve calculus/calculi located in the living body, including calculus/calculi located in the ureter (ureter stones) and calculus located in the kidneys (kidney stones), though the methods, systems and devices are not limited in this regard. The references below to calculus should be understood to refer to calculus in the singular as well as calculi in the plural.

Generally speaking, the calculus removing/retrieving device disclosed here, as represented by the several embodiments representing examples of the inventive retrieving device (and method), is configured to be positioned inside a living body at a position which will allow the retrieving device to suck-in or draw-in calculus to be retrieved. Set forth below is a detailed description of features and aspects of the calculus retrieving system, including a calculus retrieving device, and method described here by way of various embodiments representing examples of the disclosed inventions. The systems, devices and methods disclosed here for retrieving calculus have particular useful application to retrieve calculus located at places in the human body, where removal of the calculus may be difficult.

Generally speaking, the calculus retrieving device disclosed here, as characterized by the several embodiments representing examples of the inventive calculus retrieving device (and method), is configured to be positioned inside a living body, at a position adjacent the location of calculus to be retrieved from the living body and moved to a new (different) location in the living body. The calculus (stone/stones) is drawn towards the retrieving device by creating a suction force in the retrieving device. After the calculus is retrieved, the calculus is retained or held by the retrieving device, and the retrieving device is moved to the new location in the living body at which the retrieved calculus is to be repositioned. The retained calculus is subsequently released at the new location in the living body. Appropriate procedures (e.g., lithotripsy) can then be performed with respect to the calculus which has been moved Turning now to the drawing figures, FIG. 1 illustrates, in a schematic fashion, a system 20 for retrieving and moving calculus (stone or stones) located in a living body. The system 20 includes a retrieving device 30 and an elongated body 40 possessing a lumen to deliver the retrieving device 30 to the desired place in the living body. In this illustrated embodiment representing one example of the system disclosed here, the elongated body 40 is a ureteroscope. The ureteroscope includes a lumen or instrument channel 42, which receives a portion of the retrieving device 30, as will be described in more detail below. During use of the retrieving device 30, the ureteroscope 40 is introduced into the living body by way of a ureteral access sheath 24. The ureteroscope 40 passes through a lumen 28 in the ureteral access sheath 24.

Figure 2:
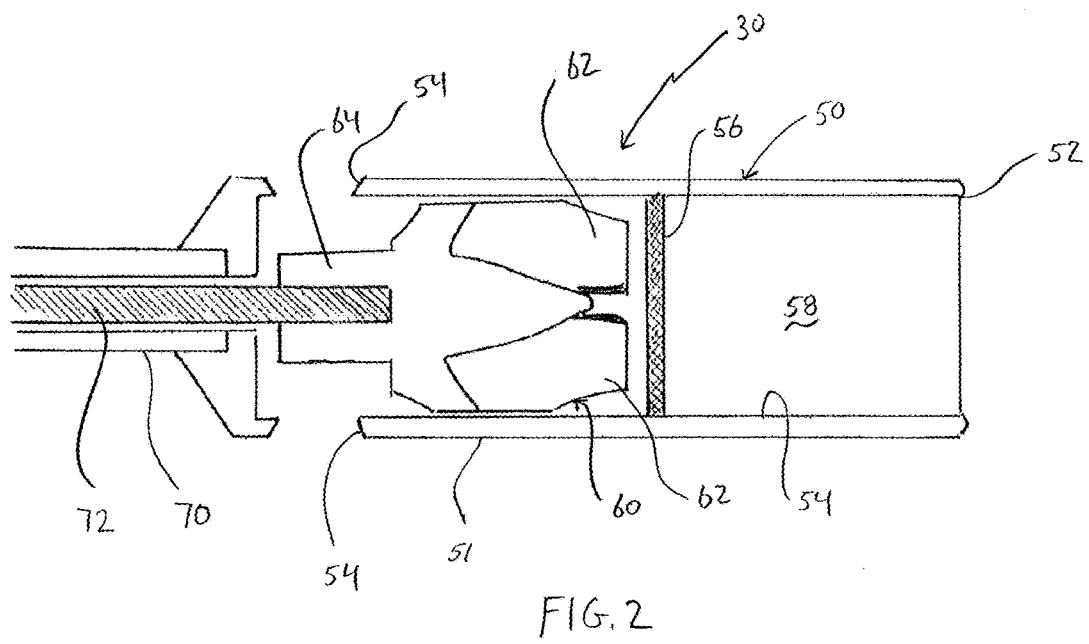
FIG. 2 is a side view, partially in cross section, of a retrieving device according to an embodiment representing an example of the retrieving device disclosed here.

Additional details and features associated with the calculus retrieving device 30 can be seen with reference to FIGS. 1, 2 and 3. The calculus retrieving device 30 includes a suction head 50 that includes an elongated body or housing 51 having an open distal end 52. The housing 51 is a tubular housing possessing a lumen 54 defining an interior of the housing 51. The housing 51 can be configured as a cylindrical elongated body or housing.

The retrieving device 30 also includes a rotatable suction-producing part located inside the housing 51. In the illustrated embodiment, the rotatable suction-producing part is in the form of an impeller 60. As shown in FIGS. 1 and 3, the impeller is positioned in the housing 51 at a location spaced away from (i.e., proximally or rearwardly) the open distal end 52. An example of the impeller 60 is illustrated in FIG. 3. The impeller 60 includes a plurality of circumferentially spaced apart fins or blades 62 that are fixed to a central hub 64. The fins or blades 62 of the impeller 60 may be twisted fins or blades. The hub 64 is fixed or connected to a rotatably driven shaft 72 so that the shaft 72 and the impeller 60 rotate together as a unit. The impeller 60 is configured so that rotation of the impeller 60 in one rotational direction produces suction in the lumen 54 (in the interior) of the housing 51, while rotation of the impeller 60 in the opposite rotational direction produces the opposite result, namely an outwardly directed force out of the lumen 54. The blades 62 of the impeller 60 shown in FIGS. 2 and 3 are preferably twisted from the distal tip of the blades 62 (radially outermost tip of the blades) toward the bottom portion of the impeller where the blades are mounted. When the direction of the impeller rotation is the same as the twist direction of the blades 62, a suction force is generated. This direction of rotation of the impeller is referred to as overspin direction.

The drive shaft 72 that is connected to the hub 64 of the impeller 60 is positioned inside of and covered by a shaft cover 70. In the illustrated embodiment, the drive shaft 72 is completely covered by the shaft cover 70. The shaft cover 70 is fixed to the housing 51 forming the suction head 50 so that movement of the shaft cover 70 results in movement of the suction head 50 (including the housing 51 and the impeller 60).

The housing 51 forming the suction head 50 includes a plurality of circumferentially spaced apart openings or through holes 54. These openings or through holes 54 are positioned closer to the proximal end of the housing 51 than the distal end of the housing 51. These openings or through holes 54 form an exhaust path during operation of the retrieving device, as will become more apparent from the description below. That is, liquid (e.g., water) which has been drawn into the housing 51 of the suction head 50 during operation of the retrieving device 30 is exhausted or discharged out of the suction head 50 by way of the openings or through holes 54.

The suction head 50 further includes a filter 56 located inside the housing 51 at a position between the distal end of the impeller 60 and the open distal end 52 of the suction head 50. This filter 56 is a disc-shaped mesh member that allows the passage of fluid (e.g., liquid such as water), while also preventing the passage of calculus which has been retrieved through operation of the retrieving device 30. The filter 56 possesses an outer periphery (outer circumferential surface) in contact with the inner periphery of the suction head 50. The filter 56 is positionally fixed within the interior of the housing 51 forming the suction head 50.

The suction head 50 also includes a retrieval space 58 located between the filter 56 and the open distal end 52 of the housing 51. As will be described in more detail below, this retrieval space 58 is configured to receive calculus which has been retrieved as a result of the operation of the retrieving device 30.

During operation of the retrieving device 30, the suction head 50 is located at a position in a living body to retrieve calculus. That is, the suction head 50 is positioned relative to the calculus to be retrieved such that during operation of the retrieving device 30, the calculus will be drawn towards (sucked towards) the suction head 50. When the suction head 50 is properly positioned relative to the calculus to be retrieved, the impeller 60 is rotatably driven through operation of a drive device connected to the drive shaft 72. The drive device rotates the drive shaft 72, which in turn rotates the impeller 60. The impeller 60 is rotatably driven in a direction to create a suction in the interior of the housing 51 that draws calculus toward the open distal end 52 of the suction head 50. The suction force created by the rotation of the impeller 60 draws relatively smaller calculus (schematically shown in FIG. 1 and identified as 68) through the open distal end 52 of the suction head and into the retrieval space 58 in the housing 51. The suction force created by the rotation of the impeller 60 can also draws relatively larger calculus into contact with the distal end of the suction head 50. That is, calculus possessing an outer dimension larger than the size of the open distal end 52 of the suction head 50 can nevertheless be drawn towards the suction head 50 and retained by the suction head 50 by creating sufficient suction force in the interior of the housing 51 that holds the relatively larger calculus in contact with the distal end of the suction head 50.

Thus, by positioning the suction head 50 in the living body so that the open distal end 52 of the suction head 50 is located at a position that will allow the calculus (i.e., calculus to be retrieved) to be drawn-into or sucked into the retrieval space 58 upon rotational operation of the impeller 60, it is possible to retrieve calculus and hold the retrieved calculus either in the retrieval space 58 or at the distal end of the suction head 50. As the impeller 60 is rotated to draw calculus toward the suction head 50, liquid (e.g., water) is drawn into the retrieval space 58 by way of the distal open end 52 of the suction head 50. This liquid is passes through the filter 56, and is exhausted or discharged outside the housing 51 of the suction head 50 through the openings or through holes 54. On the other hand, the filter 56 is sized to ensure that calculus which is drawn into the retrieval space 58 of the suction head 50, does not pass through the filter 56. The rotational operation of the impeller 60 thus causes liquid flow in which liquid enters the distal open end 52 of the suction head 50, passes through the filter 56, and exits through the through holes or openings 54 in the suction head 50. Depending upon operation of the impeller 60, the liquid exhausted through the openings or through holes 54 can also be at least partially drawn back into the interior of the suction head 50, thus creating a rather turbulent and continuous liquid cycle in which the same liquid is repeatedly drawn into the suction head, exhausted through the suction head 50, drawn into the suction head, etc. This turbulent and continuous liquid cycle can help facilitate retrieval of calculus in the retrieval space 58 of the suction head 50. This is because the suction force per rotation of the impeller is increased. In addition, the calculus tends to float, making it easier to draw-in or retrieve the calculus. When drawing-in calculus in a narrow lumen in a living body (e.g. ureter), the continuous liquid cycle helps prevent fluid surrounding calculus from drying up.

Set forth next is a description of contexts in which the system for retrieving calculus disclosed here can be used, as well as a description of a manner of operation of the system for retrieving calculus. It is sometimes necessary or desirable to break-up calculus located in a living body. For instance, calculus that is relatively small can be pulled out of the body, but if the calculus is relatively large (e.g., larger than the ureter diameter), it is not possible to remove the calculus from the living body. In such situations, it would be desirable to break-up the calculus into smaller size pieces. This can oftentimes be accomplished using lithotripsy. But circumstances may make it difficult to perform lithotripsy to break-up calculus in the living body. For example, the calculus may be located at a place where damaged tissue exists, for example in a portion of the ureter in which there is damaged tissue. Alternatively, the calculus may be located in a portion of the living body (e.g., ureter) that is rather small in size (i.e., a narrow space) and difficult to access with appropriate instrumentation and equipment for performing lithotripsy (e.g., a lower calix). The approach described here involves retrieving the calculus, moving the retrieved calculus to a new (different) location which presents a larger space (e.g., the kidney or an upper calix) to perform lithotripsy or which presents a region where there is normal (non-damaged tissue) tissue.

Figure 4:
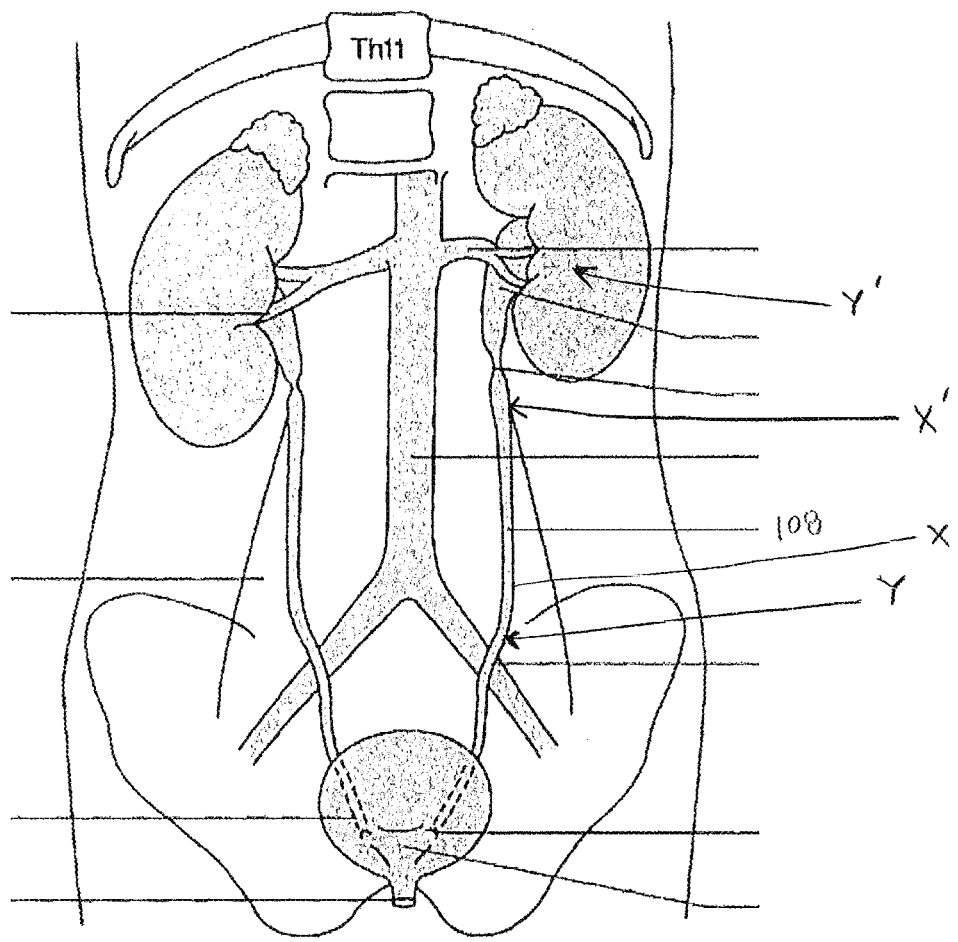
FIG. 4 is a schematic illustration of a portion of the human anatomy, including the urinary tract.

The retrieving device and system disclosed here are configured to retrieve calculus from one place in the living body, move the retrieved calculus to a new (different) place where, for example, lithotripsy can be more easily performed to break-up the calculus, and then release the retrieved and moved calculus at the new location. By way of example, and with reference to FIG. 4, it is possible to retrieve calculus at the location X in the ureter (representing an example of a region of narrow size or damaged tissue) and move the retrieved calculus to the position X' in the ureter (representing an example of a region of larger size or normal non-damaged tissue). It is also possible to retrieve calculus at the location Y (representing an example of a region of narrow size or damaged tissue) and move the retrieved calculus to the position Y' in the kidney (representing another example of a region of larger size or normal non-damaged tissue).

To retrieve and move the calculus, the retrieving system 20 shown in FIG. 6 is used. Specifically, the calculus retrieving device 30 is used, together with the operating member 26 and the ureteroscope 40. The operating member 26 is connected to the shaft cover 70, so that operation of the operating member 26 causes the shaft cover 70 to move. That is, the operation of the operating member 26 causes the shaft cover 70 to axially move, which in turn causes the suction head 50 (including the impeller 60 and the filter 56) to also axially move. FIG. 6 schematically illustrates that the shaft 72 positioned within and extending along the axel length of the shaft cover 70 is connected to a driving source 28. Operation of the driving source 28 rotates the shaft 72, which in turn rotates the impeller 60 positioned in the housing 51 of the suction head 50 of the calculus retrieving device 30. As shown in FIG. 6, the shaft cover 70 and the shaft 72 extend from the operating member 26, enter an inlet 44 of the instrument channel 42 in the ureteroscope 40, pass through the ureteroscope 40, and exit at an outlet at the distal end portion 46 of the ureteroscope 40.

In use, the shaft cover 70 is connected to the housing 51 of the suction head 50, and the proximal end of the shaft cover 70 and the shaft 72 are inserted into the outlet of the instrument channel 42 at the distal end portion 46 of the ureteroscope 40. The shaft cover 70 and the shaft 72 are pushed through the lumen (instrument channel 42) in the ureteroscope 40 until the proximal end of the shaft cover 70 and the proximal end of the shaft 72 exit out of the inlet 44 of the ureteroscope. The proximal end of the shaft 72 is then connected to the driving device 28, while the proximal end of the shaft cover 70 is fixed to the operating member 26.

The ureteroscope 40 is preferably a flexible ureteroscope. The ureteroscope 40 includes a viewing system that includes an objective lens 48 schematically illustrated in FIGS. 1 and 6. In a known manner, this provides a field of view for the user or operator to facilitate carrying out the procedure involving locating calculus, retrieving the calculus, moving the calculus to the new location and releasing the calculus at the new location.

Next, the retrieving device 30, arranged distally of the ureteroscope 40 as shown in FIG. 6, is introduced into the living body. This can be accomplished by way of the ureteral access sheath 24 schematically shown in FIG. 1. Once the retrieving device 30 is introduced into the living body, the retrieving device 30 is advanced to the desired position within the living body through operation of the operating member 26. The retrieving device 30 is preferably positioned so that the open distal end 52 of the suction head 50 is positioned near to or adjacent the calculus/calculi to be retrieved. That is, the retrieving device 30 is moved to locate the open distal end 52 at a position relative to the calculus to be retrieved such that during operation of the suction head 50 (rotation of the impeller 60), the resulting suction draws calculus toward the suction head 50.

After the suction head 50 is properly positioned relative to the calculus to be retrieved, the driving source 28 (e.g., a geared motor) is operated to rotate the impeller 60 in a direction which causes suction to be created in the interior of the suction head 50. This causes the calculus to be sucked or drawn toward the distal open end 52 of the suction head 50 and into the retrieval space 58 at the distal end portion of the suction head 50 (assuming the calculus is sufficiently small). As described above, as the calculus is drawn towards the suction head 50 (into the retrieval space 58), liquid is also drawn into the suction head 50. This liquid is able to pass through the filter 56, and is exhausted through the openings 54. On the other hand, the filter prevents the calculus which has been drawn into the retrieval space 58 from passing through the filter 56. The retrieved calculus which has entered the retrieval space thus remains in the retrieval space 58.

Figure 7A:
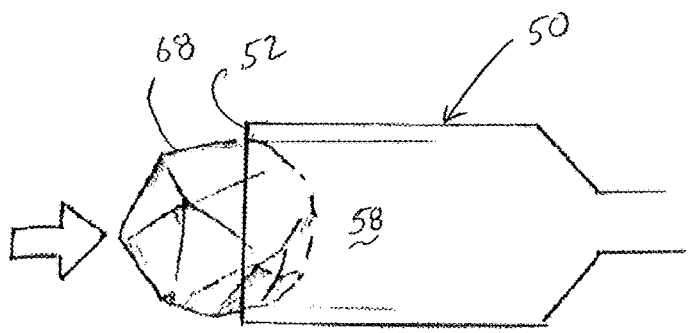
FIG. 7A illustrates an example of calculus in a living body being retrieved by the retrieving device.
Figure 7B:
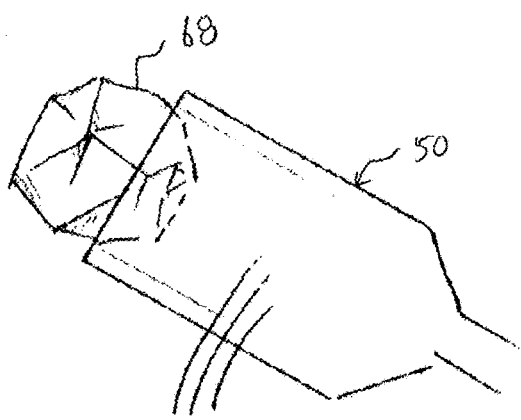
FIG. 7B is a schematic illustration of the retrieving device being moved to move the retrieved calculus to a different location in the living body.
Figure 7C:
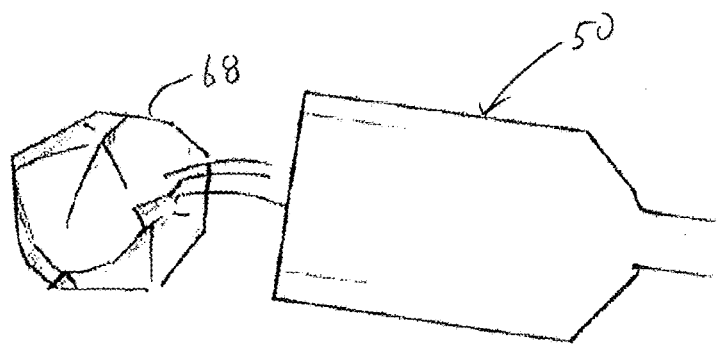
FIG. 7C is a schematic illustration of the calculus retrieving device, as the calculus previously retrieved is released.

FIGS. 7A-7C depict three aspects of the method disclosed here involving retrieving calculus 68 through operation of the suction head 50 (FIG. 7A), moving the suction head 50 and the retrieved calculus 68 to a new location (FIG. 7B), and releasing the calculus 68 (FIG. 7C). FIG. 7A generally illustrates calculus 68 that has been drawn towards the suction head 50 and is held against the open distal end 52 of the suction head 50. In this illustrated version, the retrieved calculus 68 possesses an outer dimension greater than the inner dimension of the lumen (retrieval space 58) in the suction head 50. This possibility is only for illustrative purposes, and it is to be understood that a similar operation is performed to retrieve smaller calculus that are able to pass through the open distal end 52 of the suction head and be positioned inside the retrieval space 58, such as schematically illustrated in FIG. 1.

The retrieval of the calculus 68, the retention of the calculus 68 during movement of the suction head 50, and the release of the retrieved calculus can be accomplished by controlling various operational parameters of the suction head 50. These operational parameters include the rotation operation of the impeller 60 (ON/OFF), the rotation speed of the impeller 60, and the rotation direction of the impeller. That is, by varying the rotation operation, the rotation speed and the rotation direction of the impeller 60, it is possible to control the retrieval, the retention and the release of the calculus.

During retrieval of the calculus, the impeller 60 is preferably rotated (i.e., the rotational operation is ON), is rotated at a relatively high speed (e.g., 15,000 rpm-20,000 rpm), and is rotated in the overspin direction intended to create suction in the suction head 50. The calculus 68 is thus drawn toward the open distal end 52 of the suction head 50. If the calculus 68 is smaller than the open distal end 52 of the suction head 50, the calculus 68 will enter the retrieval space 58 as shown in FIG. 1. If the calculus 68 is larger than the open distal end 52 of the suction head 50, the calculus 68 will be held against the distal end of the suction head as shown in FIGS. 7A-7C.

After the calculus 68 has been retrieved, it is necessary to retain the retrieved calculus 68 in the retrieval space 58 of the suction head 50 or against the distal end of the suction head 50 while moving the suction head 50 to transport the retrieved calculus 68 to the new (different) location. To retain the retrieved calculus 68, the driving device 28 continues to operate (i.e., the rotational operation is ON) so that the impeller 60 continues rotating. The rotation direction of the impeller 60 is the same as the rotation direction of the impeller during retrieval of the calculus. In addition, the rotation speed of the impeller 60 can be the same relatively high speed as the rotation speed of the impeller 60 during retrieval of the calculus/calculi, or can be a slightly slower rotation speed (e.g., 12,000 rpm-15,000 rpm).

While operating the suction head in the above described manner to retain the retrieved calculus 60, the suction head 50 is moved through operation of the operating member 26 to position the open distal end 52 of the suction head 50 at the new location where the retrieved calculus is to be released. When the suction head reaches this position, it is now necessary to operate the suction head 50 to release the calculus 68. To do this, the operator turns off the operation of the driving source 28 so that the retention power disappears and then the retrieved calculus 60 drops from the open distal end 52 of the suction head 50 naturally. In this rotation-OFF state, the retrieved calculus 60 retained in the retrieval space 58 can be rather easily released by small movement of the suction head 50. In the situation that the release of the calculus 68 should be controlled more exactly or accurately, or the retrieved calculi 60 are difficult to release from the retrieval space 58 because the calculi 60 may be jammed in the retrieval space 58, the operator can change the operation of the driving source 28 so that the driving source rotates the shaft 72 and the impeller 60 in the direction opposite the rotational direction of the impeller and the shaft during retrieval and retention of the calculus/calculi. That is, the impeller 60 is operated in the backspin direction. The rotational speed of the impeller 60 during release of the calculus is preferably slower than the rotational speed of the impeller 60 during retention of the calculus 68 when the suction head 50 is being moved to the new location.

After releasing the retrieved calculus 68, the retrieving device 30 is removed from the living body, or is moved to a position in the living body to retrieve other calculus.

As described above, the calculus is preferably retrieved from a portion of the living body which is not well suited to removing the calculus and which does not lend itself to the use of lithotripsy. The use of the retrieving device 30 thus allows the calculus to be retrieved and moved to another location at which lithotripsy can be used to break-up the calculus into smaller pieces so that the smaller pieces can either be removed from the body naturally or by use of appropriate instrumentation. The description above describes use of the retrieving device 30 to retrieving calculus and moving the retrieved calculus to a new location in the living body. But the retrieving device disclosed here is not limited to this manner of use. For example, it is possible to use the retrieving device 30 as an instrument for removing calculus from a living body.

Figure 9:
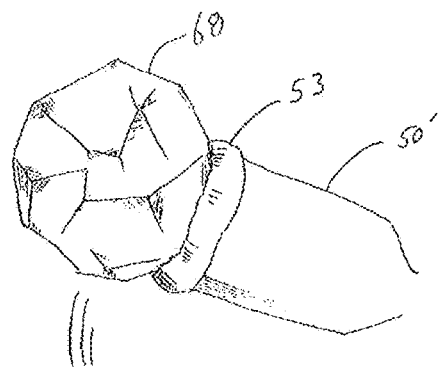
FIG. 9 is a schematic illustration of an embodiment of the retrieving device representing another example of the retrieving device disclosed here.

FIG. 9 illustrates a slight variation on the configuration of the suction head described above and illustrated in FIGS. 1, 2 and 6. The embodiment of the suction head 50' illustrated in FIG. 9 includes a gel-like material 53 that is located at the open distal end of the suction head 50'. The gel-like material 53 constitutes a compressible member 53 that helps to facilitate the retention of the calculus 68 on the suction head so that, for example, the calculus 68 does not become separated from the suction head while the calculus is being conveyed to the new location. The gel-like material 53 provides a greater area of contact with the retrieved calculus 68 than would otherwise be the case. Examples of the gel-like material 53 include silicone, soft rubber and polyurethane. The gel-like material 53 can be used when it is expected that the size of the calculus 68 being retrieved is larger than the opening at the distal end of the suction head 50'. The gel-like material can also be provided at the end of the suction head if small calculus that enter the retrieval space are being retrieved.

Another aspect of the retrieving device disclosed here is the ability of the retrieving device to retrieve calculus located in regions of the living body that are highly curved and require significant and severe manipulation to reach. The retrieving device includes a particularly configured shaft cover 70 covering the shaft 72. As described above, the distal end of the shaft cover 70 is connected or fixed to the suction head. FIG. 1 generally illustrates the configuration of the shaft cover 70, while FIG. 8 illustrates the configuration of the shaft cover in more detail.

Figure 8:
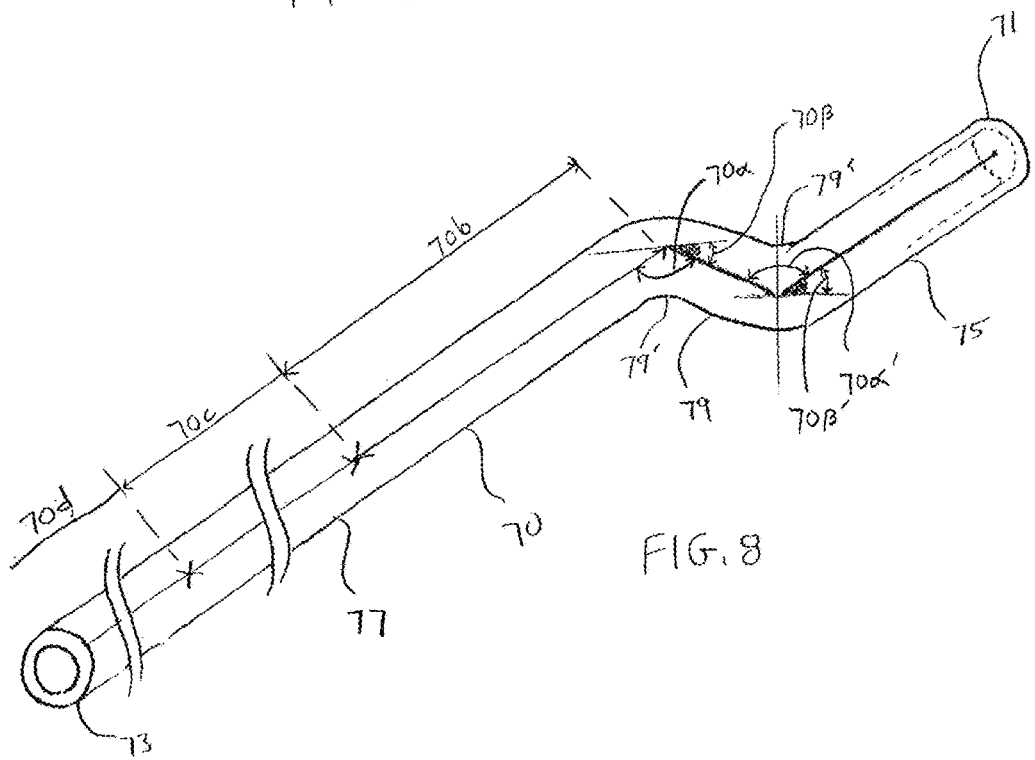
FIG. 8 is a prospective view of the shaft cover forming a part of the retrieving device shown in FIG. 1.

Referring to FIG. 8, The shaft cover 70 includes a distal section 75, a proximal section 77 and an intermediately located bent section 79 positioned between the distal section 75 and the proximal section 77. In the illustrated embodiment, the distal section 75 and the proximal section 77 are linearly extending (straight) sections. The intermediately located bent section 79 is bounded on opposite ends by respective bends 79'. The distal section 75 extends from the distal end 71 of the shaft cover 70 to the intermediately located bent section 79, and the proximal section 77 extends from the proximal end 73 of the shaft cover 70 to the intermediately located bent section 79. The bent section 79 is a stiff bent section, meaning that if the bent section 79 is not surrounded by or influenced by a rigid lumen, the bent section 79 is always bent, by virtue of the bends 79', relative to the proximal section 77 and the distal section 75. That is, in the absence of a force or load (external or internal) applied to the bent section, the bent section 79 remains bent. On the other hand, when the bent section 79 is inserted into or positioned in the instrument channel 42 of the ureteroscope, a force or load is applied to the bent section 79 by the straight instrument channel 42 and so the shape of the section 79 is changed from bent to straight (i.e., the bent section 79 is straightened out). When the bent section 79 located in the instrument channel 42 of the ureteroscope is pulled out of the instrument channel 42, the bent section 79 automatically returns to its bent configuration.

The distal end 71 of the shaft cover 70 is connected or fixed to the suction head 50 while the proximal end 73 of the shaft cover 70 is connected to the operating member 26. In the illustrated embodiment, the central axis of the distal section 75 and the central axis of the proximal section 77 are parallel to one another, but offset from one another so that the proximal section 77 and the distal section 75 are not coaxial.

FIG. 8 shows that the proximal section 77 of the shaft cover 70 includes three portions, namely the distal portion 70b of the proximal section 77, the intermediate portion 70c of the proximal section 77, and the proximal portion 70d of the proximal section 77. The distal portion 70b of the proximal section 77 is preferably made of a material that is relatively stiff or rigid. The purpose for this relatively stiff or rigid material is to keep the tip positioned position so that the suction head 50 does not bow under its own weight. Appropriate material can be rubber or plastic material. The intermediate section 79 and the distal section 75 of the shaft cover 70 are preferably also made of relatively stiff or rigid material. The intermediate section 79 and the distal section 75 of the shaft cover 70 can be fabricated from the same material forming the distal portion 70b of the proximal section 77.

The intermediate portion 70c of the proximal section 77 is preferably made of a relatively soft material. The material forming the intermediate portion 70c of the proximal section 70 is softer than the material forming the distal portion 70b of the proximal section 77. The material forming the intermediate portion 70c of the proximal section 77 is thus a material that is more flexible than the relatively stiff or rigid material forming the distal section 70b of the proximal section 77. In other words, the intermediate portion 70c of the proximal section 77 is more flexible than the distal portion 70b of the proximal section 77. The purpose of this material is to help prevent the intermediate portion of the proximal section from negatively impacting the ability of the ureteroscope to deflect.

The proximal portion 70d of the proximal section 77 is made of a relatively stiff or rigid material that is specifically selected to ensure appropriate torque transmission. That is, the material forming the proximal portion 70d is preferably selected so that torque applied to the proximal portion of the proximal section (e.g., by way of the operating member 26) is appropriately transmitted toward the distal section of the shaft cover 70. The stiffness of the proximal portion 70d is preferably greater than the stiffness of the distal portion 70b.

To provide an example of the relative lengths of the portions 70b, 70c, 70d forming the proximal section 77 of the cover shaft, the distal portion 70b of the proximal section 77 is preferably 6 mm-15 mm in length, more preferably 8 mm in length, the intermediate portion 70c is preferably 60 mm-150 mm in length, more preferably 80 mm in length and the proximal portion 70d of the proximal section 77 is preferably 800 mm-1200 mm in length, more preferably 1000 mm in length. Thus, the distal portion 70b of the proximal section 77 is shorter than the intermediate portion 70c and the proximal portion 70d of the proximal section 77, and the intermediate portion 70c is shorter than the proximal portion 70d of the proximal section 77. In addition, the intermediate section can possess a length of preferably 1 mm-3 mm, more preferably approximately 2 mm while the distal section 75 possesses a length of preferably 3 mm-8 mm, more preferably about 5 mm.

As described above, the intermediately located bent section 79 is bounded on opposite ends by bends 79', 79'. As will be described in more detail below, the bends 79', 79' are preferably configured so that during use, the suction head 50 of the retrieval device 30 is angled at an angle of at least 25° relative to the central axis of the distal end portion of the ureteroscope 40. To achieve this result, the angles 70α, 70α' illustrated in FIG. 8 are preferably 120° while the angles 70β, 70β' are 30°.

Figure 10A:
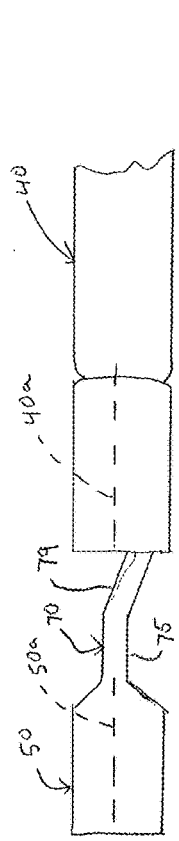
FIG. 10A is a side view of the retrieving device outfitted with the shaft cover shown in FIG. 8 according to one operational aspect.

Connecting the suction head to a shaft cover 70 possessing the configuration shown in FIG. 8 imparts the following operational characteristics to the retrieving device. FIG. 10A illustrates the shaft cover 70 connected to the suction head 50, while the proximal portion 70d of the proximal section 77, the intermediate portion 70c of the proximal section 77 and a part of the distal portion 70b of the proximal section 77 are located in the instrument channel of the ureteroscope 40. The distal section 75 of the shaft cover 70, the intermediately located bent section 79 of the shaft cover 70 and a part of the distal portion 70b of the proximal section 77 of the shaft cover 70 are positioned outside the ureteroscope 40 as shown in FIG. 10A. In this position, the central axis 50a of the suction head 50 is parallel to, and offset from, the central axis 40a of the distal end portion of the ureteroscope 40. The coaxial arrangement of the suction head 50 relative to the ureteroscope 40 is used when advancing the retrieving device through the living body in regions that are not highly curved.

Starting at the position shown in FIG. 10A, axially moving (pulling) the shaft cover 70 in the proximal direction (i.e., moving the shaft cover 70 in the rearward direction indicated by the rightward arrow in FIG. 10A) causes the remaining part of the distal portion 70b of the proximal section 77 of the cover shaft to enter the instrument channel 42 in the ureteroscope 40, and also causes a part of the bent section 79 of the shaft cover 70 to enter the instrument channel 42 in the ureteroscope 40. The retrieval device 30 thus takes on the arrangement or configuration shown in FIG. 10B.

Figure 10B:
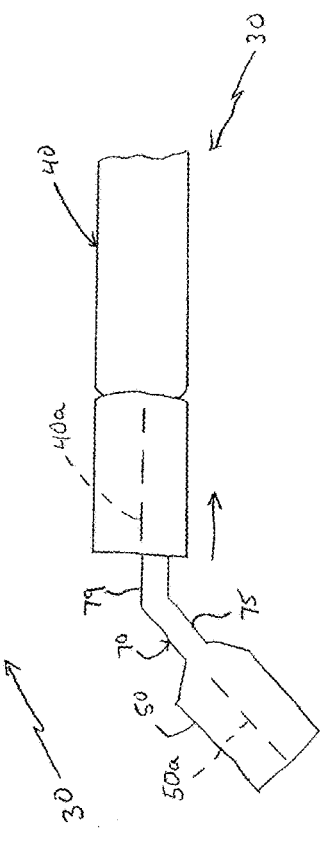
FIG. 10B illustrates the retrieving device according to another operational aspect after moving the suction head in the rearward direction to orient the suction head at an angle relative to the elongated body.

As shown in FIG. 10B, axially moving a portion of the bent section 79 of the shaft cover 70 into the instrument channel in the ureteroscope 40 causes the suction head 50 to be angled relative to the ureteroscope 40. In particular, the central axis 50a of the suction head 50 is oriented at an angle (i.e., an angle other than 0° and 180°) relative to the central axis 40a of the distal end portion of the ureteroscope 40. The angle between the central axis 50a of the suction head 50 and the central axis 40a of the ureteroscope 40 is preferably at least 25°, more preferably at least 30°. Angling the suction head 50 relative to the ureteroscope 40 in this manner allows the suction head 50 to access highly curved regions in a living body that might otherwise be very difficult to access with the suction head orientation shown in FIG. 10A.

Figure 5:
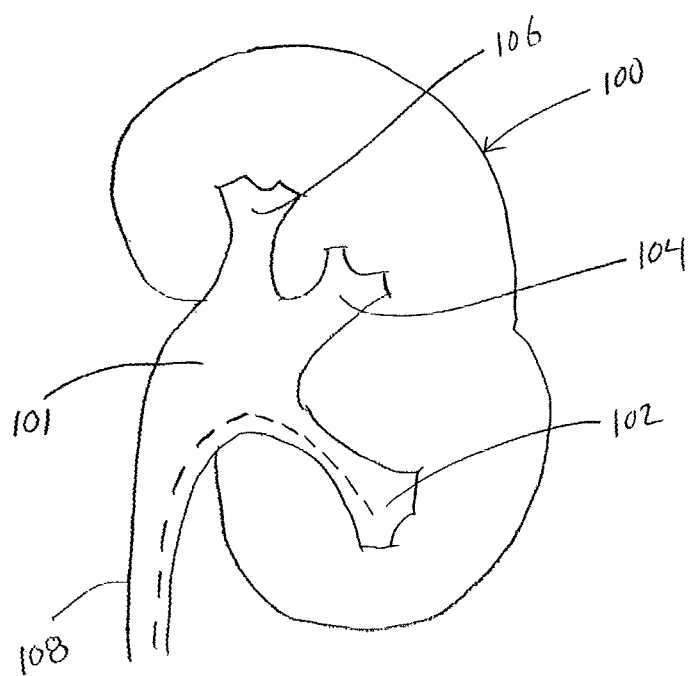
FIG. 5 is an schematic illustration of a human kidney.

As an example, reference is made to the FIG. 5 schematic illustration of a kidney possessing a lower calix (lower renal calix) 102, a middle or intermediate calix (middle or intermediate renal calix) 104, an upper calix (upper renal calix) 106, and a renal pelvis 101 spaced from the calices 102, 104, 106. To reach calculus in the lower calix 102 requires access by way of the ureter 108 along a path generally indicated by the dotted line FIG. 5. As can be readily appreciated, this path is highly curved and can be difficult to navigate.

Configuring the retrieval device 30 to include the shaft cover 70 illustrated in FIG. 8, it is possible to angle the suction head 50 of the retrieval device 30 relative to the ureteroscope 40 in the manner illustrated in FIG. 10B by axially moving the shaft cover in the rearward direction, thus making it easier to traverse or navigate the path indicated by the dotted line in FIG. 5. It is thus possible to retrieve calculus in the lower calix 102 and move the retrieved calculus/calculi to the middle or intermediate calix 104 or possibly the upper calix 106. Lithotripsy can then be more easily carried out with respect to the retrieved and moved calculus.

Figure 10C:
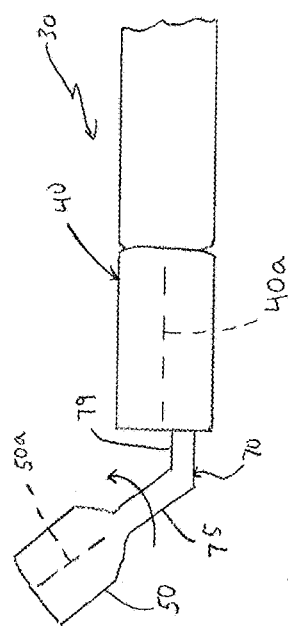
FIG. 10C illustrates the retrieving device shown in FIG. 10A according to another operational aspect in which the suction head is rotated 180° from the position shown in FIG. 10B.

FIG. 10C illustrates the retrieval device 30 in a position that is the same as shown in FIG. 10B, except that the shaft cover 70 is rotated so that the suction head 50 is angled at an orientation 180° relative to the orientation shown in FIG. 10B. In the position shown in FIG. 10C, the suction head 50 is angled relative to the ureteroscope 40 so that the angle between the central axis 50a of the suction head 50 and the central axis 40a of the ureteroscope 40 is preferably at least 25°, more preferably at least 30°. There are benefits associated with being able to rotate the shaft cover 70 and the suction head 50 from the FIG. 10B position to the FIG. 10C position. An ureteroscope is typically equipped with the ability to deflect, but the manner of bending is typically somewhat limited. That is, the movement of the tip portion of the ureteroscope is limited to one plane (uniplanar movement or X-plane movement). It is thus difficult for an operator to freely control the direction or orientation of the suction head relying only on the ureteroscope deflection ability. On the other hand, when the operator rotates the angled suction head from FIG. 10B to FIG. 10C, the different plane of movement of the suction head (y-plane movement) is added to the plane of movement ability of the ureteroscope. Further, if the operator pushes/pulls the shaft cover 70, a still further movement direction is added (z-plane). That is why the operator can control the direction of the suction head freely by rotation (between FIG. 10B and FIG. 10C) of the angled-suction head. From another point of view, the installation location of an objective lens of the ureteroscope is off-center. So if the operator rotates the angled suction head from the FIG. 10B position to the FIG. 10C position, operator can change the view of the suction head 50.

Figure 10D:
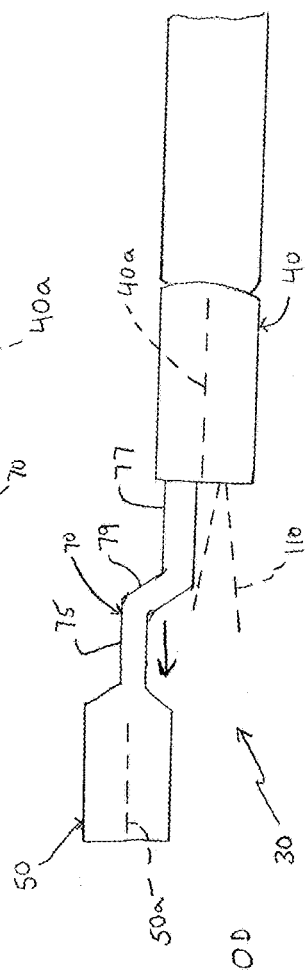
FIG. 10D illustrates the retrieving device shown according to an further operational aspect in which the suction head is moved forwardly to position the suction head at a location permitting viewing, by way of the ureteroscope.

FIG. 10D illustrates the retrieving device in which the shaft cover 70 and the suction head 50 are axially moved in the forward direction (i.e., to the right, as indicated by the arrow, in FIG. 10D). This causes the suction head 50 to move axially forward, and shift to a position in which the central axis 50a of the suction head 50 is parallel to and offset (not coaxial) from the central axis 40a of the distal end portion of the ureteroscope 40. This permits a field of view 100 for the operator using the optical system in the ureteroscope 40.

Figure 10E:
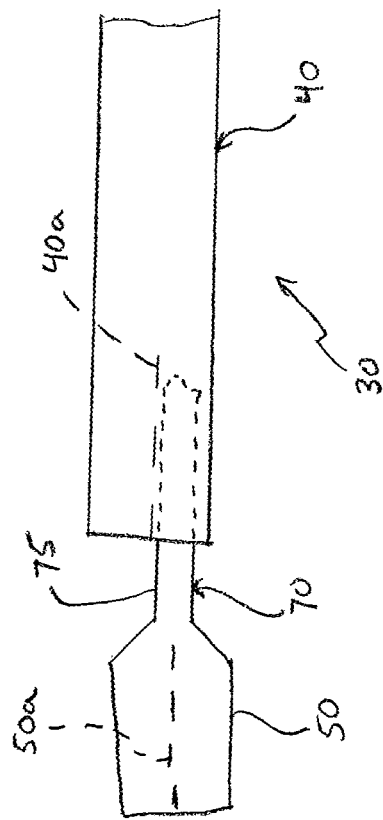
FIG. 10E illustrates the retrieving device according to an further operational aspect in which the shaft cover is pulled from the position shown in FIG. 10B.

FIG. 10E illustrates another operational aspect of the retrieving device 30. With the retrieving device 30 in the position shown in FIG. 10B (or FIG. 10C), the operator can axially pull-back the shaft cover 70 (i.e., move the shaft cover 70, together with the suction head 50 and the shaft 72) so that the shaft cover 70 is moved into the elongated body 40 (ureteroscope), to straighten the bent section 79. The total length of the tip portion of the device (the suction head+the exposed or uncovered portion of the shaft cover 70+the unbendable distal end portion of the ureteroscope) is shorter compared to the total length of the tip portion in FIG. 10B. The operational position of the retrieving device shown in FIG. 10E is advantageous when moving or maneuvering the retrieving device into a narrow lumen (e.g., an ureter and an ureteral access sheath).

Figure 11A:
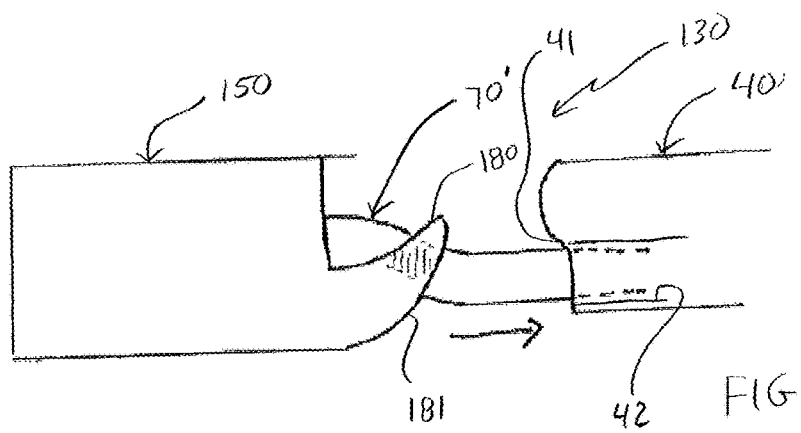
FIG. 11A is a side view of an embodiment of the retrieving device representing another example of the retrieving device disclosed here in which the retrieving device is configured to angle the suction head relative to the ureteroscope.
Figure 11B:
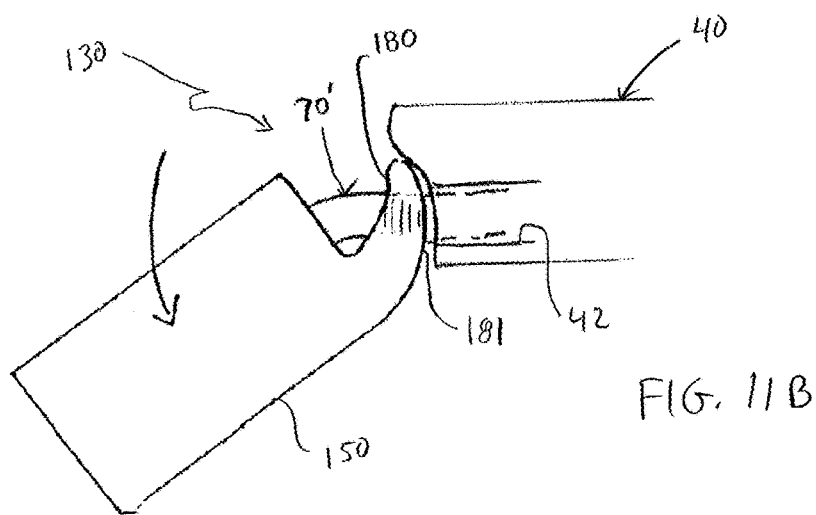
FIG. 11B illustrates the retrieving device according to another operational aspect after moving the suction head in the rearward direction so that the suction head is angled relative to the ureteroscope.
Figure 11C:
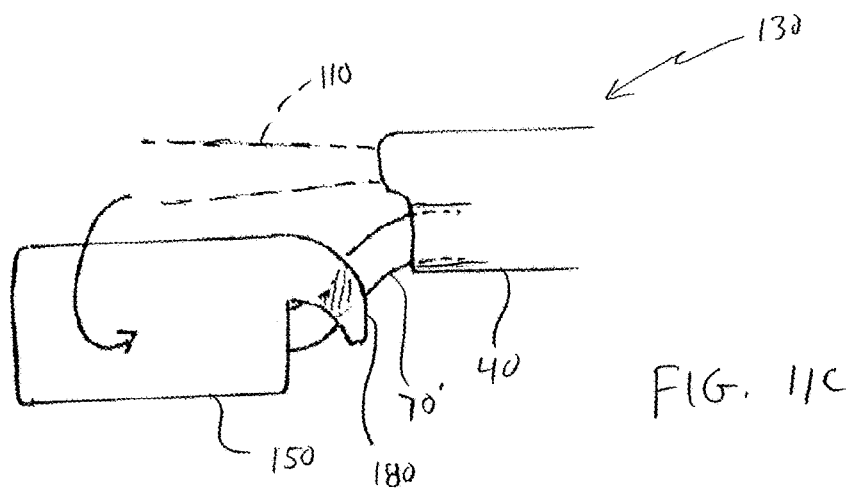
FIG. 11C illustrates the retrieving device shown in FIG. 11A according to another operational aspect in which the suction head is rotated 180° from the position shown in FIG. 11A.

FIGS. 11A-11C illustrates an embodiment representing another example of the inventive retrieving device disclosed here. The embodiment shown in FIGS. 11A-11C represents an alternative way of angling the suction head relative to the distal end portion of the ureteroscope. This embodiment of the retrieving device depicted in FIGS. 11A-11C is similar to the embodiment described above and illustrated in FIGS. 10A-10D, except that the angling of the suction head is facilitated by a shaped contact part rather than a shaped tube.

Referring to FIG. 11A, a contact part 180 is provided between the suction head 150 and the ureteroscope 40. In this embodiment, the contact part 180 is integrally formed in one piece at the same time with the suction head 150. The contact part 180 projects rearwardly (in the proximal direction) away from the suction head 150 as illustrated in FIG. 11A. The contact part 180 in this embodiment is a curved projecting portion. The contact part 180 includes a curved surface 181, namely a convex surface. The retrieval device 130 further includes a shaft cover 70' is a linearly extending (straight) shaft cover 70'. FIG. 11A shows that the shaft cover 70' passes through a hole in the contact part 180 so that the contact part 180 at least partially surrounds the shaft cover 70'.

The shaft cover 70' passes through a hole in the contact part 180 at an angle in FIG. 11A so that the central axis of the suction head 150 and the central axis of the distal end portion of the shaft cover 70' are parallel to one another, but offset from one another so that the suction head 150 and the distal end portion of the shaft cover 70' are not coaxial with one another. This offset contributes to angling the suction head by the shaped contact part in FIGS. 11-16. The suction head 150 and the distal end portion of the ureteroscope 40 shown in FIG. 11A are oriented in the manner shown in FIG. 11A while advancing the retrieval device 130 within the narrow lumen (e.g., an ureter or an ureteral access sheath). To manipulate or move the retrieval device through a relatively narrow lumen or to retrieve calculus in a narrow lumen, the operator tends to choose or may prefer the device being in the state shown in FIG. 11A. To manipulate or move the retrieval device through a curved area (e.g., to reach a lower calix (lower renal calix)), the operator tends to choose or may prefer the device being in the state depicted in FIG. 11B. To retrieve calculus in a large area (e.g., an open space in kidney), the operator can use the device positioned in either the state shown in FIG. 11A or the state shown in FIG. 11B.

To angle the suction head 150 relative to the distal end portion of the ureteroscope 140, at first the shaft cover 70' is axially moved or pulled rearwardly (i.e., to the right, in the direction of the arrow, in FIG. 11A) until the contact part 180 comes into direct contact with the curved (concave) distal end surface 41 of the ureteroscope 40. In this state (the curved surface of the contact part 180 just contacts the distal end surface 41 of the ureteroscope 40), the suction head 150 is not angled. As the shaft cover 70' continues to be axially moved in the rearward direction, this contact between the two curved surfaces 181, 41 helps cause the suction head 150 to become angled relative to the distal end portion of the ureteroscope 40 as illustrated in FIG. 11B. It is thus possible to angle the suction head 50 relative to the ureteroscope 40 by axially moving the shaft cover (and the suction head 50).

From the position illustrated in FIG. 11A, it is possible to rotate the suction head 150 by rotating the shaft cover 70'. The suction head 150 is moved to the position shown in FIG. 11C which is displaced 180° from the position shown in FIG. 11A. In the position of the suction head 150 shown in FIG. 11A, the suction head 150 and the distal end portion of the ureteroscope 40 are parallel and coaxial with one another. By rotating the suction head 150 to the FIG. 11A position, the operator can pass the retrieval device 130 into a relatively narrow lumen (e.g. a ureter and a ureteral access sheath). In the position of the suction head 150 shown in FIG. 11C, the suction head 150 does not obstruct the field of view 110 seen through the objective lens of the ureteroscope 40. By rotating the suction head 150 in this way, the medical professional can observe in front of the retrieval device 130 to help facilitate the procedure.

Figure 12A:
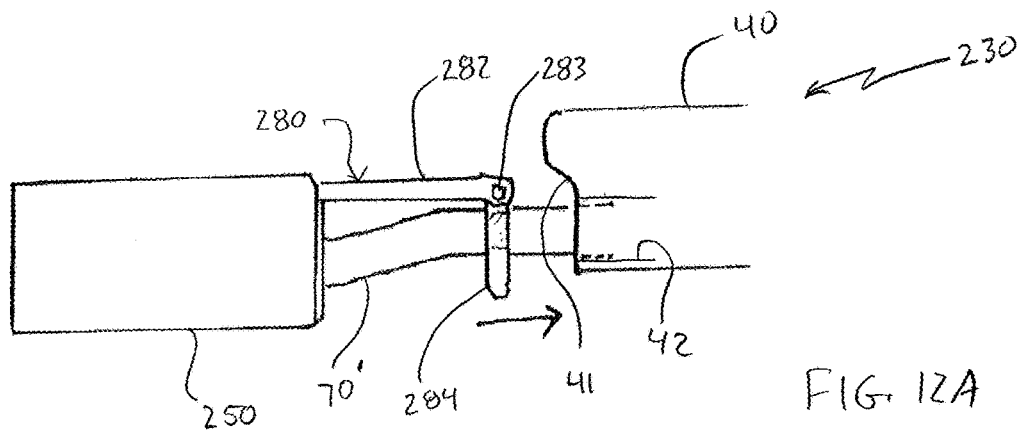
FIG. 12A is a side view of an embodiment of the retrieving device representing an additional example of the retrieving device disclosed here in which the retrieving device is configured to angle the suction head relative to the ureteroscope.
Figure 12B:
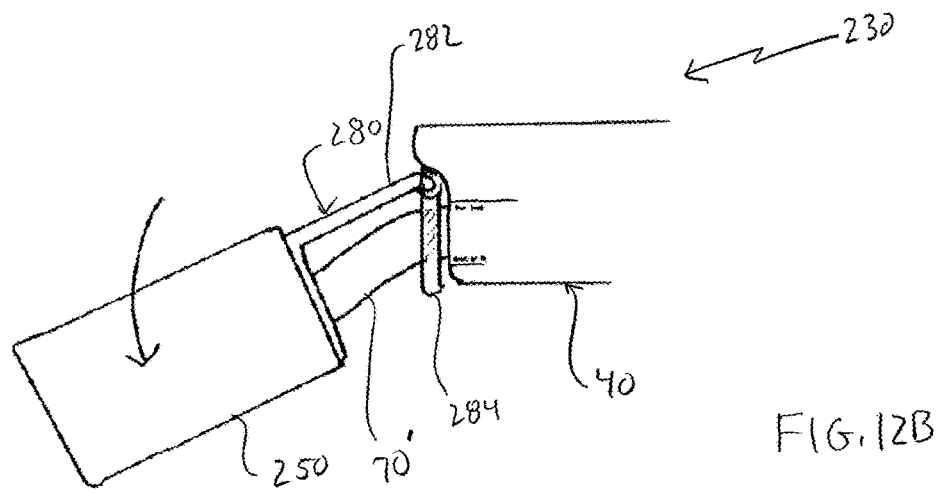
FIG. 12B illustrates the retrieving device according to another operational aspect after moving the suction head in the rearward direction so that the suction head is angled relative to the ureteroscope.

FIGS. 12A and 12B illustrate another embodiment. This embodiment of the retrieval device 230 is similar to the embodiment illustrated in FIGS. 11A-11C, except that the configuration of the contact part is different. The embodiment of the retrieval device 230 shown in FIGS. 12A-12B includes a contact part 280 that includes two sections 282, 284 connected to one another by a hinge 283. The two sections 282, 284 can be plate-shaped elements. One of the sections 282 is fixed to or integral with the suction head 250, and the other section 284 possesses a through hole through which the shaft cover 70' passes. The section 284 thus partially surrounds the shaft cover 70'. The shaft cover 70' is a linearly extending (straight) shaft cover 70'

In operation, the shaft cover 70' is moved axially in the rearward direction (i.e., to the right, in the direction of the arrow, in FIG. 12A) and the contact part 280 approaches the curved (concavely curved) distal end surface 41 of the ureteroscope 40 and ultimately contacts the concavely curved distal end surface 41 of the ureteroscope 40. After the section 282 of the contact part contacts the concavely shaped distal end surface of the ureteroscope 40, continued axial movement of the shaft cover 70' in the proximal or rearward direction causes the suction head 250 to become angled relative to the distal end portion of the ureteroscope as shown in FIG. 12B. In this way, the central axis of the suction head 250 forms an angle (i.e., an angle other than 0° and 180°) relative to the central axis of the distal end portion of the ureteroscope 40. The suction head 250 is preferably angled at an angle of at least 25° relative to the central axis of the distal end portion of the ureteroscope 40, more preferably at least 30°. The section 284 can help stabilize the contact between the section 282 and the distal end surface of the ureteroscope 40.

Figure 13A:
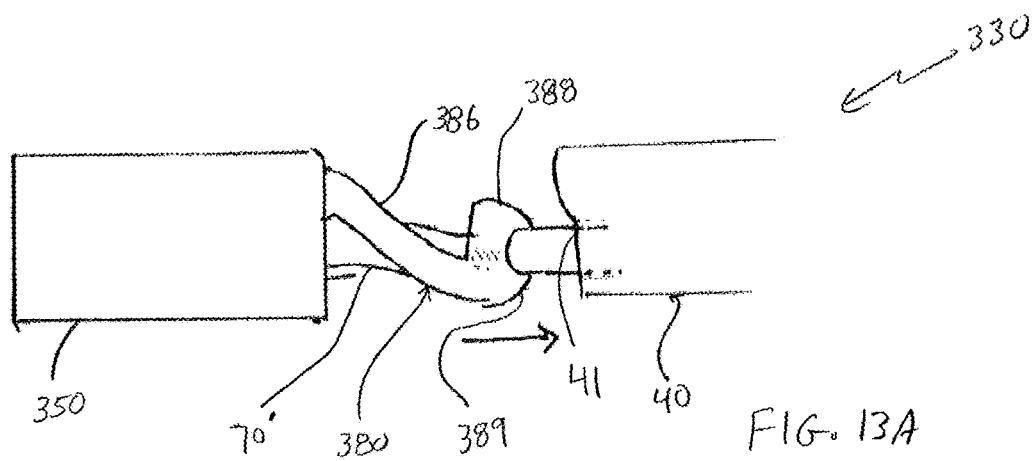
FIG. 13A is a side view of an embodiment of the retrieving device representing another example of the retrieving device disclosed here in which the retrieving device is configured to angle the suction head relative to the ureteroscope.
Figure 13B:
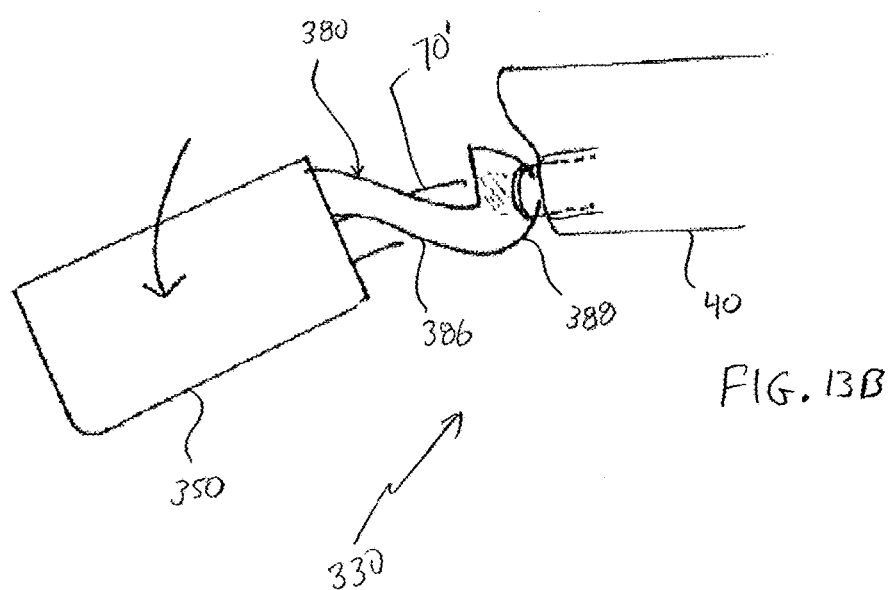
FIG. 13B illustrates the retrieving device according to another operational aspect after moving the suction head in the rearward direction so that the suction head is angled relative to the ureteroscope.

FIGS. 13A and 13B illustrate an embodiment representing another example of the retrieving device disclosed here in which the retrieving device is configured to angle the suction head relative to the ureteroscope. This embodiment of the retrieving device differs from the version shown in FIGS. 12A and 12B in that the contact part 380 is a rigid one-piece member. The contact part 380 is integrally formed in one piece with the suction head 350, but can also be separate from the suction head 350 and fixed in place to the suction head 350. The contact part 380 includes an arm 386 projecting away from the suction head 350, and a hemispherical portion 388 configured to contact the concave curved distal end surface 41 of the ureteroscope 40. The hemispherical shaped portion 388 presents a convex surface that directly contacts the concave curved distal end surface 14 of the ureteroscope 40. The hemispherical shaped portion 388 of the contact part 380 includes a through hole or opening through which passes the shaft cover 70' so that a portion of the contact part 380 encircles or surrounds the shaft cover 70'. The shaft cover 70' is a linearly extending (straight) shaft cover 70'

In use, the shaft cover 70' is axially moved in the rearward direction (i.e., to the right, in the direction of the arrow, in FIG. 13A). This causes the suction head 350 and the contact portion 380 to also move in the rearward direction until the hemispherical shaped portion 388 directly contacts the distal end surface of the ureteroscope 40. Continued rearward axial movement of the shaft cover 70' causes the suction head 350 to pivot in the manner indicated by the arrow in FIG. 13B so that the suction head 350 is angled relative to the ureteroscope 40. That is, the central axis of the suction head 350 is angled at an angle of at least 25°, preferably at least 30°, relative to the central axis of the distal end portion of the ureteroscope 40.

Figure 14A:
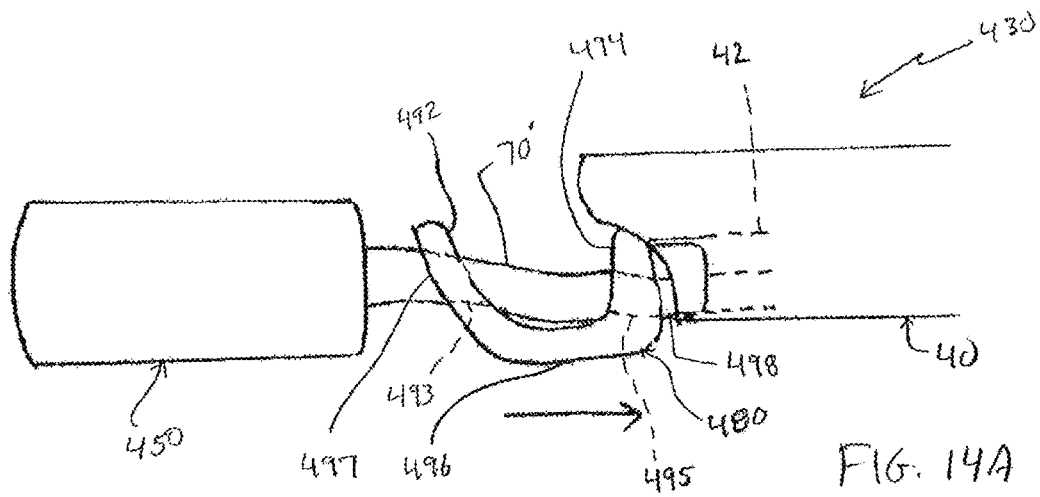
FIG. 14A is a side view of an embodiment of the retrieving device representing a further example of the retrieving device disclosed here in which the retrieving device is configured to angle the suction head relative to the ureteroscope.
Figure 14B:
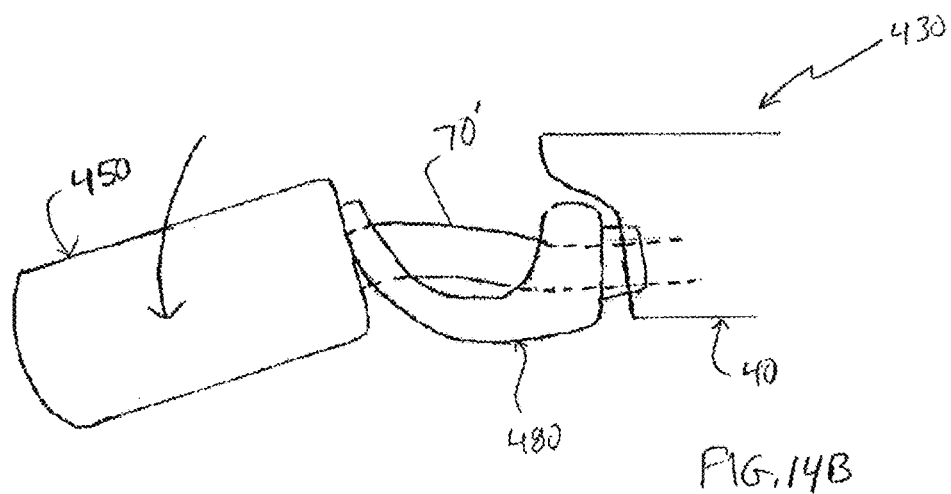
FIG. 14B illustrates the retrieving device according to another operational aspect after moving the suction head in the rearward direction so that the suction head is angled relative to the ureteroscope.

FIGS. 14A and 14B illustrate an embodiment representing a further example of the retrieving device disclosed here in which the retrieving device is configured to angle the suction head relative to the ureteroscope. This embodiment of the retrieving device 430 utilizes a contact part 480 that is separate from both the suction head 450 and the ureteroscope 40, but is subsequently mounted on or connected to the distal end portion of the ureteroscope 40. The contact part 480 is a generally U-shaped member defined by two spaced-apart legs 492, 494 connected by an intermediately located base 496. The leg 492 closest to the suction head includes a curved surface 497 facing towards the suction head. A hollow cylindrical element 498 is integrally formed with one of the legs 494 and projects away from the leg 494. The cylindrical element 498 is positioned in the instrument channel 42 at the distal end portion of the ureteroscope 40 so that the contact part 480 is integrated with and held in the ureteroscope 40.

Each of the legs 492, 494 of the contact part 480 is provided with a through hole 493, 495 through which passes the shaft cover 70'. The shaft cover 70' is a linearly extending (straight) shaft cover 70'. By virtue of the through holes 493, 495 in the legs 492, 494 of the contact part 480, a portion of the contact part 480 surrounds the shaft cover 70 at two spaced apart locations. The shaft cover 70' forming a part of the retrieval device 430 shown in FIGS. 14A and 14B is a linearly extending (straight) tube. The shaft cover 70' passes through holes 493 and/or 495 in the contact part 180 at an angle as shown in FIG. 14A so that the central axis of the suction head 450 and the central axis of the distal end portion of the shaft cover 70' are parallel to one another, but offset from one another so that the suction head 450 and the distal end portion of the shaft cover 70' are not coaxial.

In use, the contact part 480 is fitted to the ureteroscope 40 by positioning the cylindrical element 498 in the instrument channel 42 at the distal end portion of the ureteroscope 40. The shaft cover 70' is then axially moved in the proximal direction (i.e., to the right, in the direction of the arrow, in FIG. 14A). This causes the suction head 450 to approach the ureteroscope 40 and eventually move into direct contact with the curved surface 497 on the leg 492 of the contact part 480. As the shaft cover 70' continues to be axially moved (pulled) in the proximal direction, the suction head 450 becomes angled by virtue of the curved surface 497 of the leg 492 of the contact part 480 contacting the suction head 450 so that the suction head 450 becomes angled with respect to the ureteroscope.

Figure 15A:
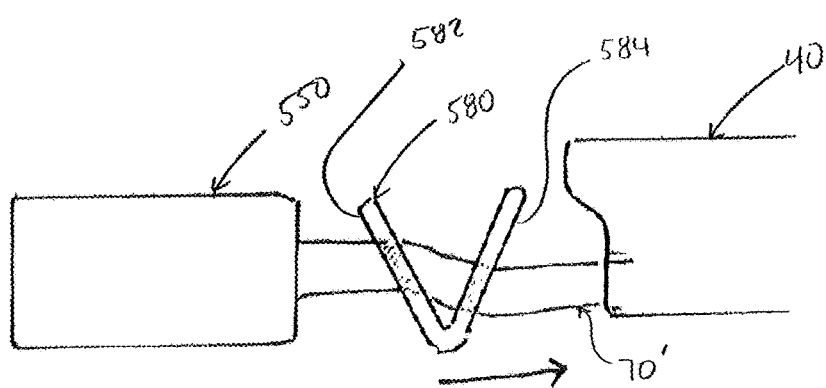
FIG. 15A is a side view of an embodiment of the retrieving device representing another example of the retrieving device disclosed here in which the retrieving device is configured to angle the suction head relative to the ureteroscope.
Figure 15B:
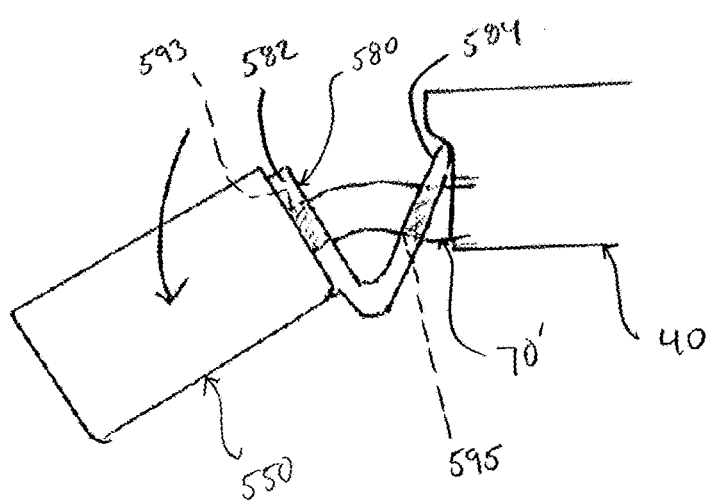
FIG. 15B illustrates the retrieving device according to another operational aspect after moving the suction head in the rearward direction so that the suction head is angled relative to the ureteroscope.

FIGS. 15A and 15B illustrate an embodiment of the retrieving device representing another example of the inventive retrieving device disclosed here. This embodiment of the retrieving device 530 includes a contact part 580 that is separate from both the suction head 550 and the ureteroscope 40. The contact part 580 is a generally V-shaped one-piece contact part that includes two legs 582, 584 connected to one another at a vertex. The two legs 582, 584 diverge away from one another in a direction away from the vertex. Each of the legs 582, 584 includes a respective through hole 593, 595 through which extends the shaft cover 70'. A portion of the contact part 580 thus encircles or surrounds the shaft cover 70' at two spaced apart locations. The shaft cover 70' is a linearly extending (straight) shaft cover 70'.

In use, the shaft cover 70' is axially moved in the proximal direction (i.e., to the right, in the direction of the arrow, in FIG. 15A). This causes the suction head 550 to also move in the proximal direction. Eventually, the suction head 550 contacts the leg 582 of the contact part 580, and the leg 584 of the contact part 580 contacts the distal end of the ureteroscope 40. As the shaft cover 70' continues to be axially moved (pulled) in the proximal direction, the suction head 550 becomes angled by V-shaped contact part 580 contacting both the suction head 550 and the distal end of the ureteroscope 40 so that the suction head 550 becomes angled with respect to the ureteroscope 40 in the manner illustrated in FIG. 15B. That is, the suction head 550 moves in the direction of the arrow in FIG. 15B so that the central axis of the suction head 550 is disposed at an angle (other than 0° and 180°) relative to the central axis of the distal end portion of the ureteroscope 40. That is, the central axis of the suction head 550 is angled at an angle of at least 25°, preferably at least 30°, relative to the central axis of the distal end portion of the ureteroscope 40.

It is possible to control the angle of inclination of the suction head 550 relative to the ureteroscope 40 in the embodiment shown in FIGS. 15A and 15B by appropriately selecting the material forming the contact part 580. For example, the contact part 580 can be made of a relatively rigid material, like metal, so that the two legs 582, 584 are relatively stiff and maintain the relative position/orientation when the leg 582 is contacted by the suction head 550 and the leg 584 contacts the distal end of the ureteroscope 40. On the other hand, the contact part 580 can be made of a more flexible material such that in the arrangement shown in FIG. 15B, continued axial movement of the shaft cover 70' in the proximal or rearward direction varies the angle between the suction head 550 and the ureteroscope 40.

Figure 16A:
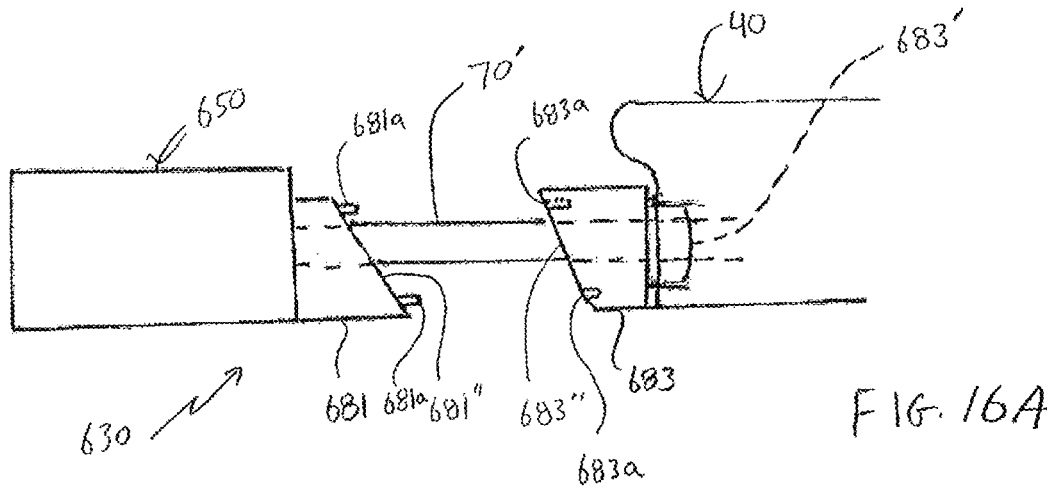
FIG. 16A is a side view of an embodiment of the retrieving device representing another example of the retrieving device disclosed here in which the retrieving device is configured to angle the suction head relative to the ureteroscope.
Figure 16B:
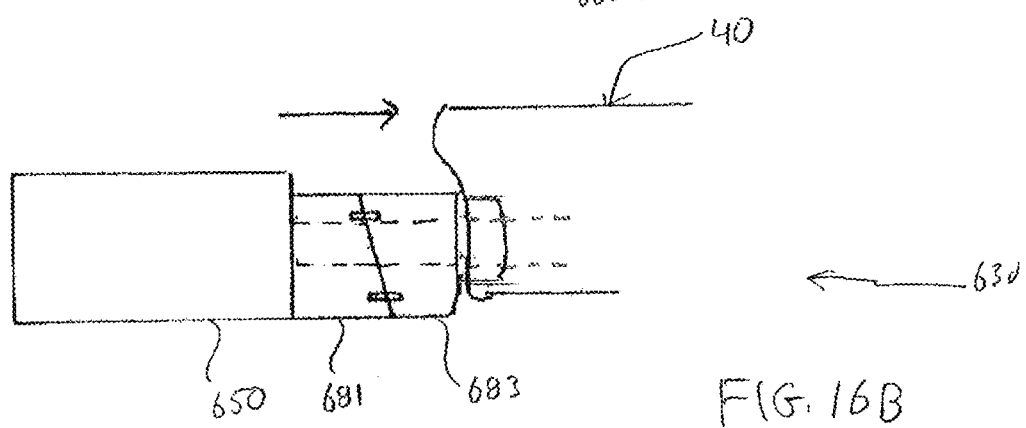
FIG. 16B illustrates the retrieving device according to another operational aspect after moving the suction head in the rearward direction.
Figure 16C:
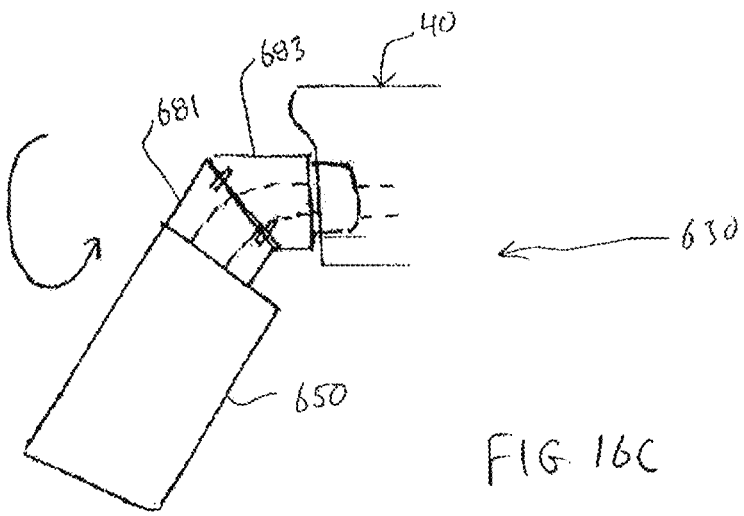
FIG. 16C illustrates the retrieving device shown in FIG. 16B according to another operational aspect in which the suction head is rotated 180° from the position shown in FIG. 16C.

FIGS. 16A-16C illustrate an embodiment representing another example of the retrieving device disclosed here. This embodiment of the retrieving device 630 provides another mechanism for angling the suction head 650 relative to the ureteroscope 40. This embodiment includes a contact part comprised of two separate contact sections 681, 683. The first contact section 681 is connected to or fixed to the suction head 650 so that the first contact section 681 and the suction head 650 move together as a unit, while the second contact section 683 includes a cylindrical-shaped projection 683' that fits into the instrument channel at the distal end portion of the ureteroscope 40 so that the second contact section 683 and the suction head 650 move together as a unit. The second contact section 683 is thus integrated with or connected to the ureteroscope 40. The first and second contact sections 681, 683 each include a respective inclined face or surface 681", 683". Each of these first and second contact sections 681, 683 also includes a through hole or opening through which extends the shaft cover 70'. In this embodiment, the shaft cover 70' is a linearly extending (straight) shaft cover 70'. Each of the contact sections 681, 683 thus encircles a portion of the shaft cover 70'.

Two projections 681a, 681a project from the inclined surface 681" of the first contact section 681 toward the second contact section 683. Two recesses 683a, 683a are provided in the inclined surface 683" of the second contact section 683. Each of the recesses 683a, 683a is configured to receive one of the projections 681a, 681a projecting from the first contact part 681.

In use, the shaft cover 70' is axially moved in the proximal direction (i.e., in the rearward direction, indicated by the arrow, in FIG. 16B) so that the suction head 650 approaches the ureteroscope 40. Eventually, each of the projections 681a, 681a projecting from the first contact section 681 enters the respective recess 683a, 683a in the second contact section 683 as shown in FIG. 16B. The suction head 650 and the ureteroscope 40 are thus locked together (rotationally locked together). In the arrangement shown in FIG. 16B, the retrieval device 630 is moved through the relatively narrow lumen of the living body toward the desired location.

To angle the suction head 650 relative to the distal end portion of the ureteroscope 40, the first and second contact sections 681, 683 are separated from one another so that the projections 681a, 681a are separated (spaced) from the respective recess 683a. The first contact section 681 is rotated 180° relative to the second contact section 683 as illustrated by the arrow in FIG. 16C. This can be accomplished by rotating the shaft cover 70' and the suction head 650 relative to the ureteroscope 40. After rotating the first contact section 681, the projections 681a, 681a projecting from the first contact section 681 are fitted into respective recesses in the second contact section 683 as illustrated in FIG. 16C. In the angled orientation shown in FIG. 16C, the recesses in the second contact part 683 that receive the projections 681a, 681a differ from (i.e., are angled differently than) the recesses 683a, 683a shown in FIG. 16A.

This embodiment of the retrieving device 630 provides a fixed angular orientation between the central axis of the suction head 650 and the central axis of the distal end portion of the ureteroscope 40. This angular orientation is defined by the angle of the inclined faces 681", 683" of the first and second contact sections 681, 683. It is possible to adjust the angular orientation by changing the angle of inclination of the inclined surfaces 681", 683".

Each of the embodiments of the retrieving device disclosed above for angularly orientating the suction head relative to the distal end portion of the ureteroscope 40 makes it possible to angularly position the suction head by axially moving the shaft cover and the suction head relative to the ureteroscope. It is thus possible to achieve a desired angular orientation of the suction head without excessive effort and without a complicated construction.

The detailed description above describes a device and method for retrieving/removing calculus from parts of a living body such as the ureter and the renal pelvis. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of retrieving calculus in a living body and relocating the calculus to a different location in the living body, the method comprising:

positioning an elongated member, which includes a suction head disposed on a distal side of the elongated member, in the living body in which the calculus is located;

drawing the calculus in the living body toward the suction head while the suction head is positioned in the living body so that the calculus is retained by the suction head;

moving the suction head so that the suction head is located at a position in the living body that is different from the position of the suction head in the living body during the drawing of the calculus toward the suction head;

releasing the calculus from the suction head so that the calculus is at a position in the living body different from a location of the calculus in the living body while the calculus is being drawn toward the suction head;

the drawing of the calculus toward the suction head comprises rotating an impeller positioned inside the suction head in a first rotational direction;

the releasing of the calculus from the suction head comprises: i) rotating the impeller positioned inside the suction head in a second rotational direction which is opposite the first rotational direction; or ii) rotating the impeller positioned inside the suction head at a rotation speed slower than the rotation speed of the impeller during the drawing of the calculus toward the suction head; and the drawing of the calculus toward the suction head comprising rotating the impeller positioned inside the suction head at a first speed and in a first rotational direction, wherein the impeller continues to rotate in the first rotational direction during the moving of the suction head, and wherein the releasing of the calculus from the suction head comprises rotating the impeller at a second rotational speed less than the first rotational speed.

2. The method according to claim 1, wherein the rotating of the impeller creates a suction that draws the calculus into a hollow retrieval space in the suction head and retaining the calculus in the hollow retrieval space during the moving of the suction head.

3. The method according to claim 1, wherein the drawing of the calculus toward the suction head comprises rotating the impeller positioned inside the suction head in a first rotational direction, and the releasing of the calculus from the suction head comprises rotating the impeller positioned inside the suction head in a second rotational direction which is opposite the first rotational direction.

4. The method according to claim 1, wherein the suction head possesses a distal end at which is located a compressible material, the distal end opening into an interior of the suction head, and wherein the calculus is retained by the suction head at a position at least partially outside the interior of the suction head by being held against the compressible material.

5. The method according to claim 1, wherein the positioning of the suction head in the living body comprises positioning the suction head in a kidney, wherein the drawing of the calculus toward the suction head comprises drawing calculus located in a lower calix of the kidney toward the suction head so that the calculus is retained by the suction head, and wherein the releasing of the calculus from the suction head comprises releasing the calculus retained by the suction head at either an upper calix or a middle calix of the kidney.

6. The method according to claim 1, wherein the suction head passes through an instrument channel in a ureteroscope and extends distally beyond a distal end portion of the ureteroscope, the distal end portion of the ureteroscope possessing a central axis and the suction head possessing a central axis, and further comprising operating the suction head so that the central axis of the suction head is at an angle other than 0° and other than 180° relative to the central axis of the distal end portion of the ureteroscope.

7. The method according to claim 1, wherein the suction head passes through an instrument channel in a ureteroscope and extends distally beyond a distal end portion of the ureteroscope, the distal end portion of the ureteroscope possessing a central axis and the suction head possessing a central axis, and further comprising operating the suction head so that the central axis of the suction head is at an angle of at least 25° relative to the central axis of the distal end portion of the ureteroscope.

8. A method of retrieving calculus in a living body and relocating the calculus to a different location in the living body, the method comprising:

positioning a suction head, disposed on a distal end of a shaft, in the living body in which the calculus is located, the suction head possessing a central axis, the shaft being positioned in a lumen in an elongated member, the elongated member being located in the living body and possessing a distal end;

relatively moving the suction head and a first contact surface so that a second contact surface that is fixed to and moves together with suction head contacts the first contact surface while the suction head and the second contact surface are located outside the lumen at a position distal of the distal end of the elongated member, the contact of the second contact surface with the first contact surface changing an orientation of the central axis of the suction head to orient the suction head in an orientation permitting retrieval of the calculus in the living body;

drawing the calculus in the living body toward the suction head while the suction head is positioned in the living body and after changing the orientation of the central axis of the suction head so that the calculus is retained by the suction head;

moving the suction head so that the suction head is located at a position in the living body that is different from the position of the suction head in the living body during the drawing of the calculus toward the suction head; and releasing the calculus from the suction head so that the calculus is at a position in the living body different from a location of the calculus in the living body while the calculus is being drawn toward the suction head.

9. The method according to claim 8, wherein the elongated member is a ureteroscope, wherein the suction head passes through an instrument channel in the ureteroscope and extends distally beyond the distal end of the ureteroscope, the first contact surface being a distal end surface of the ureteroscope.

10. The method according to claim 9, wherein the first and second contact surfaces are both curved surfaces.

11. The method according to claim 9, wherein the first contact surface is a concave surface and the second contact surface is a convex surface.

12. The method according to claim 8, wherein the first and second contact surfaces are both curved surfaces.

13. The method according to claim 8, wherein one of the first and second contact surfaces is a concave surface and the other of the first and second contact surfaces is a convex surface.

14. The method according to claim 8, wherein the drawing of the calculus toward the suction head comprises rotating an impeller positioned inside the suction head, the impeller being connected to a drive shaft so that rotation of the shaft results in rotation of the impeller, the drive shaft passing through an instrument channel in a ureteroscope, the suction head possessing a central axis and a distal end portion of the ureteroscope possessing a central axis;

the method further comprising rotating the suction head relative to the distal end of the ureteroscope between a first position in which the central axis of the suction head is parallel to and coaxial with the central axis of the ureteroscope and a second position in which the central axis of the suction head is parallel to and not coaxial with the central axis of the ureteroscope.

15. The method according to claim 8, wherein the positioning of the suction head in the living body comprises positioning the suction head in a kidney, wherein the drawing of the calculus toward the suction head comprises drawing calculus located in a lower calix of the kidney toward the suction head so that the calculus is retained by the suction head, and wherein the releasing of the calculus from the suction head comprises releasing the calculus retained by the suction head at either an upper calix or a middle calix of the kidney.

16. A method of retrieving calculus in a living body and relocating the calculus to a different location in the living body, the method comprising:

positioning an elongated member, which includes a suction head disposed on a distal side of the elongated member, in the living body in which the calculus is located, the elongated member being positioned in a lumen in a ureteroscope, the ureteroscope possessing a distal end portion, the distal end portion of the ureteroscope and the suction head each possessing a respective central axis;

drawing the calculus in the living body toward the suction head while the suction head is positioned in the living body and while the suction head is distal of the lumen in the ureteroscope so that the calculus is retained by the suction head;

moving the suction head so that the suction head is located at a position in the living body that is different from the position of the suction head in the living body during the drawing of the calculus toward the suction head;

releasing the calculus from the suction head so that the calculus is at a position in the living body different from a location of the calculus in the living body while the calculus is being drawn toward the suction head;

changing an angular orientation of the central axis of the suction head relative to the central axis of the distal end portion of the ureteroscope; and the changing of the angular orientation of the central axis of the suction head relative to the central axis of the distal end portion of the ureteroscope comprises relatively moving a suction head contact surface that is fixed to and moves together with the suction head and an other contact surface to cause the suction head contact surface to contact the other contact surface in a way that causes the orientation of the central axis of the suction head relative the central axis of the distal end portion of the ureteroscope to change, the suction head contact surface contacting the other contact surface while the suction head and the suction head contact surface are positioned outside the lumen in the ureteroscope.

17. The method according to claim 16, wherein at least one of the suction head contact surface and the other contact surface is a curved surface.

18. The method according to claim 16, wherein at least one of the suction head contact surface and the other contact surface is a convex surface.

19. The method according to claim 16, wherein the other contact surface is an exterior surface of the ureteroscope at a distal end surface of the ureteroscope.

* * * * *